(12) United States Patent
Weissman et al.

(10) Patent No.: US 9,957,576 B2
(45) Date of Patent: May 1, 2018

(54) METHODS FOR DETERMINING RESPONSIVENESS TO AN ANTI-CD47 AGENT

(71) Applicant: The Board of Trustees of the Leland Stanford Junior University, Stanford, CA (US)

(72) Inventors: Irving L. Weissman, Stanford, CA (US); Victor Albert Eng, San Francisco, CA (US); Rahul Sinha, Los Altos, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days. days.

(21) Appl. No.: 15/491,381

(22) Filed: Apr. 19, 2017

(65) Prior Publication Data

US 2017/0306413 A1    Oct. 26, 2017

Related U.S. Application Data

(60) Provisional application No. 62/325,940, filed on Apr. 21, 2016.

(51) Int. Cl.
| | | |
|---|---|---|
| *C12Q 1/68* | (2006.01) | |
| *C07K 16/28* | (2006.01) | |
| *A61K 39/00* | (2006.01) | |

(52) U.S. Cl.
CPC ........ *C12Q 1/6886* (2013.01); *C07K 16/2803* (2013.01); *A61K 2039/505* (2013.01); *C07K 2317/76* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | |
|---|---|---|
| 7,767,410 B2 | 8/2010 | Weissman et al. |
| 8,232,071 B2 | 7/2012 | Weissman et al. |
| 9,017,675 B2 | 4/2015 | Liu et al. |
| 9,151,760 B2 | 10/2015 | Weissman et al. |
| 9,382,320 B2 | 7/2016 | Liu et al. |
| 2008/0187950 A1 | 8/2008 | Weissman et al. |
| 2010/0226927 A1 | 9/2010 | Weissman et al. |
| 2010/0255575 A1 | 10/2010 | Weissman et al. |
| 2012/0225073 A1 | 9/2012 | Weissman et al. |
| 2013/0142786 A1 | 6/2013 | Liu et al. |
| 2014/0271683 A1 | 9/2014 | Chao et al. |
| 2015/0183874 A1 | 7/2015 | Liu et al. |
| 2016/0008429 A1 | 1/2016 | Willingham et al. |
| 2016/0069898 A1 | 3/2016 | Weiskopf et al. |
| 2016/0144009 A1 | 5/2016 | Tseng et al. |
| 2016/0194406 A1 | 7/2016 | Leeper et al. |
| 2016/0289326 A1 | 10/2016 | Chao et al. |
| 2016/0304609 A1 | 10/2016 | Liu et al. |
| 2017/0029524 A1 | 2/2017 | Liu et al. |
| 2017/0066834 A1 | 3/2017 | Weissman et al. |
| 2017/0073414 A1 | 3/2017 | Weiskopf et al. |

FOREIGN PATENT DOCUMENTS

| | | |
|---|---|---|
| WO | 2008/067115 A2 | 6/2008 |
| WO | 2008/073316 A2 | 6/2008 |
| WO | 2011/041453 A1 | 4/2011 |
| WO | 2011/143624 A2 | 11/2011 |
| WO | 2012/088309 A1 | 6/2012 |
| WO | 2014/149477 A1 | 9/2014 |
| WO | 2014/179132 A1 | 11/2014 |
| WO | 2014/186761 A2 | 11/2014 |
| WO | 2015/041987 A1 | 3/2015 |
| WO | 2015/138600 A2 | 9/2015 |
| WO | 2015/161267 A2 | 10/2015 |
| WO | 2016/022971 A1 | 2/2016 |
| WO | 2016/044021 A1 | 3/2016 |
| WO | 2016/065329 A1 | 4/2016 |
| WO | 2016/138306 A1 | 9/2016 |
| WO | 2016/179399 A1 | 11/2016 |
| WO | 2016/205042 A1 | 12/2016 |
| WO | 2017/035480 A1 | 3/2017 |

OTHER PUBLICATIONS

Reinhold et al (Journal of Cell Science, 1995, 108: 3419-3425).*
Willingham et al (PNAS, 2012, 109(17): 6662-6667).*
Yoshida et al (Cancer Med, 2015, 4(9): 1322-1333).*
Chao et al (Cancer Res, 2011, 71(4): 1374-1384).*

* cited by examiner

*Primary Examiner* — Sean E Aeder
(74) *Attorney, Agent, or Firm* — Pamela J. Sherwood; Bozicevic, Field & Francis LLP

(57) ABSTRACT

Methods and kits are provided for determining whether an individual is responsive to an anti-CD47 agent by assaying biological samples for the level or ratio of isoforms of CD47 in the sample.

6 Claims, 10 Drawing Sheets
(10 of 10 Drawing Sheet(s) Filed in Color)

FIG. 2A
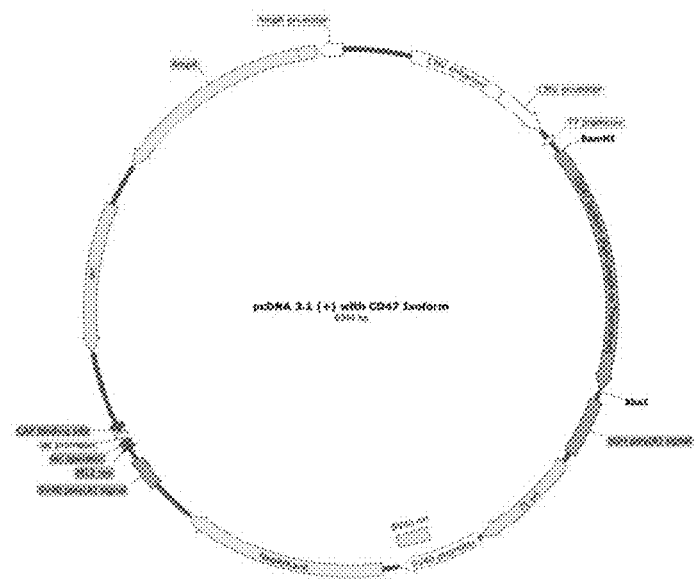
FIG. 2B
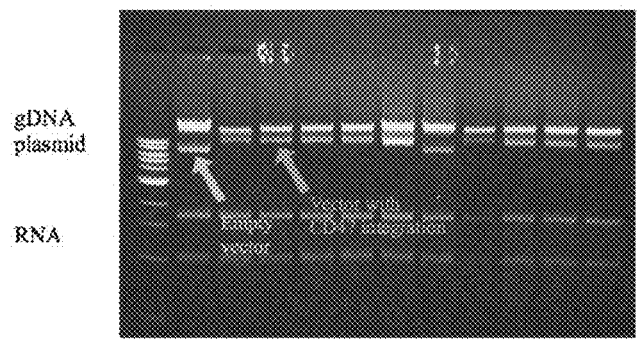
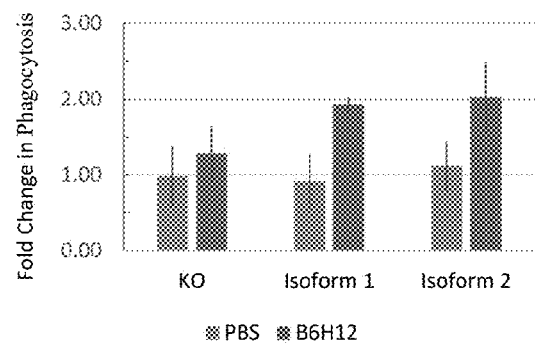
FIG. 2C

METHODS FOR DETERMINING RESPONSIVENESS TO AN ANTI-CD47 AGENT

CROSS REFERENCE

This application claims benefit of U.S. Provisional Patent Application No. 62/325,940, filed Apr. 21, 2016, which application is incorporated herein by reference in its entirety.

BACKGROUND OF THE INVENTION

Immune evasion is a hallmark of cancer, and antibodies that block the binding of CD47 protein to the SIRPα increase clearance of cancer cells by the immune system. CD47 is ubiquitously expressed at low levels on the surface of normal cells. It typically serves as a marker of self—a "don't-eat-me" signal—such that immune cells do not engulf and kill host cells. As cells age, get damaged, or become diseased, they turn on various "eat-me" signals and lose the CD47 "don't-eat-me" signal. Macrophages, a surveillance component of the innate immune system, recognize the up-regulated "eat-me" signals and eliminate those aberrant cells. Normal cells, which generally do not express these pro-phagocytic or "eat-me" signals, are protected from this immune surveillance.

Similar to aging and damaged cells, cancerous cells also express "eat-me" signals, primarily through cell-surface calreticulin. Cell-surface calreticulin exposes the cancer cells of many solid tumors to macrophages. The binding of calreticulin (an "eat-me" signal) to its LRP1 receptor on macrophages induces phagocytosis. However, cancer cells are a special class of diseased cells that are able to inhibit and avoid phagocytosis by macrophages due of an ability to turn on and amplify the dominant CD47 "don't-eat-me" signal. The progression from normal cell to cancer cell involves changes in genes and/or gene expression that trigger programmed cell death (PCD) and programmed cell removal, the two obstacles that cancer cells must overcome to survive. Many of the required steps in cancer progression subvert the multiple mechanisms of PCD, but, to date, only one step is known to be essential to subvert programmed cell removal—the expression of the dominant "don't-eat-me" signal, CD47.

In multiple preclinical studies, CD47 has been identified as an anti-phagocytic signal that is highly expressed on all types of human primary cancers investigated thus far. CD47 may be an indispensable means by which cancer cells overcome the intrinsic expression of their "eat-me" signals that result from genetic and/or epigenetic changes. Binding of CD47 to SIRPα, an inhibitory receptor on macrophages, counteracts the "eat me" signal from calreticulin and resultantly blocks phagocytosis. The CD47-SIRPα interaction results in phosphorylation of immunoreceptor tyrosine-based inhibitory motifs (ITIMs) on the cytoplasmic tail of SIRPα and the recruitment of SHP-1 and SHP-2 phosphatases, which is thought to block phagocytosis by preventing myosin-IIA accumulation at the phagocytic synapse.

Antibodies that block the binding of CD47 to its inhibitory SIRPα receptor on macrophages increase phagocytosis of cancer cells by mouse or human macrophages in vitro. Additionally, anti-CD47 antibody-mediated phagocytosis by macrophages enables presentation of intracellular proteins as peptides by MHC-I surfaces molecules to TCRs on $CD8^+$ T cells, resulting in activation of cytotoxic T cells. Usage of patient tumor xenotransplantation mouse models has also found that CD47-blocking antibodies can not only inhibit or eliminate primary tumor growth, but also prevent and eliminate metastasis. Interestingly, some cancer cells are able to escape phagocytosis even after anti-CD47 antibody treatment. Further, anti-CD47 antibody binding to chronic lymphocytic leukemia (CLL) cells has also been able to directly induce cell death in the absence of macrophages. Because CD47 is overexpressed in all cancer types, antibodies that block CD47 have the potential to enable the patient's immune system to identify and destroy all primary or metastatic cancer cells. However, the observed differential response of cancer cells to anti-CD47 antibody treatment has yet to be examined.

SUMMARY OF THE INVENTION

Methods are provided for determining whether a cell or population of cells is responsive to an anti-CD47 agent, and may further comprise methods for treatment in accordance with the determination. The methods are also useful in quantitating the aggressiveness and metastatic capability of the cell. In the subject methods, biological samples isolated from an individual are assayed to determine the CD47 isotype expressed in the cells, where the isotype correlates with responsiveness to the administration of an anti-CD47 agent. In some embodiments, a cell determined to be of a responsive type is treated with an anti-CD47 agent. In some embodiments, the methods of the invention find use in determining whether to continue or alter therapy, where a cell or population responsive to administration of an anti-CD47 agent may be treated with the same. In some such embodiments, the individual is being treated with an anti-CD47 agent for cancer. In other embodiments the individual is being treated with an anti-CD47 agent for infection, particularly with an intracellular pathogen.

Two prominent CD47 splice-variants, the full-length isoform (isoform1) and the shortest isoform (isoform2) that lacks a cytoplasmic tail, were analyzed by stably expressing them individually in cancer lines lacking endogenous CD47 expression. Isoform 2 is widely expressed in all cells and the response to blocking therapies is relatively minor. Expression of Isoform 1 can be an indication of malignant cells with a more aggressive, mesenchymal phenotype and thus have increased proliferation and metastatic capacity. The response of Isoform 1 to blocking therapies is much stronger.

In other embodiments, specific and efficacious anti-CD47 therapies are provided that selectively block isoform 1 by targeting the intracellular, cytoplasmic tail. In some such embodiments the therapy is based on the nucleotide sequence encoding the cytoplasmic sequence, e.g. RNAi, anti-sense RNA and the like. In other embodiments a screen is performed of small molecule drug candidates to select for a specifically targeted agent.

Any biological sample can be assayed to determine the CD47 isotype. Suitable biological samples include: a blood sample, a serum sample, a plasma sample, a biopsy sample, a fine needle aspirate, a lymph node aspirate, a cystic aspirate, a paracentesis sample, a thoracentesis sample, and the like. In some cases, the level of protein is measured. In some cases, the level of mRNA is measured.

An anti-CD47 agent for use in the methods of the invention interferes with binding between CD47 present on a target cell, including without limitation a cancer cell, a cell infected with an intracellular pathogen, a stem cell, etc., to SIRPα present on a phagocytic cell. Generally both such cells are present in the individual being treated. Such methods, in the presence of a pro-phagocytic signal, can increase phagocytosis of the target cell. The subject methods can be used to monitor the treatment of an individual for any disease susceptible to blockade of CD47-mediated SIRPα signaling. Suitable anti-CD47 agents include soluble SIRPα polypeptides; soluble CD47; anti-CD47 antibodies, anti-SIRPα, antibodies, small molecules, and the like, where the term antibodies encompasses antibody fragments and variants thereof, as known in the art.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

(FIG. 1A) Known CD47 isoforms as downloaded from the NCBI GeneBank. (FIG. 1B) Ethidium bromide-stained agarose gel following RT-PCR, showing relative levels of five different CD47 isoforms in two different cell lines, MOLM13 & THP1. (FIG. 1C) Schematics of the genomic fragment of CD47 spanning exon 7-11. The arrows represent the position of primers used for RT-PCR. (FIG. 1D) Ethidium bromide-stained agarose gel of RT-PCR on exons 7-11 of CD47 in multiple acute myeloid leukemia cancer cell lines. (FIG. 1E) Top: Schematic of CD47 alternative splicing. Full-length isoform in green, truncated isoform in red. Below: Full-length isoform with cytoplasmic tail on left. Truncated isoform without cytoplasmic tail on right.

FIG. 2A-2C. (FIG. 2A) pcDNA 3.1 (+) plasmid vector cloned with CD47 full-length or truncated isoform. (FIG. 2B) Phenol-chloroform nucleic acid extraction from StbI3 bacterial colonies transformed with pcDNA 3.1 (+) plasmids with CD47 isoform inserts. Bacterial colonies with upshift in plasmid weight were candidates for further sequencing. (FIG. 2C) Phagocytosis assay of DLD1 KO transfected with blank pcDNA, full-length CD47 isoform, or truncated CD47 isoform. Data is normalized to DLD1 KO transfected with blank pcDNA plasmid with no antibody treatment.

(FIG. 3A) DLD1 cells after CD47 knockout were sorted for low GFP and low CD47 surface expression as stained by B6H12 antibody. (FIG. 3B) DNA alignment of CD47 CDS with candidate DLD1 knockout reveals a 5-base pair insertion within exon 2 causing frameshift.

(FIG. 4A) Lentiviral constructs with PgK promoter, CD47 isoform, HCV/IRES, Zsgreen(GFP), T2A, and luciferase. (FIG. 4B) CD47 surface expression after lentiviral transduction of DLD1 CD47KO cells. Areas P6, P7, and P8 represent sort gates for high, medium, and low expression populations. (FIG. 4C) CD47 expression of DLD1 sorted for high, medium, and low CD47 expression after multiple weeks of propagation.

(FIG. 5A) Representation of gating for phagocytosis data collection. Green represent uneaten cancer cells. Red represents macrophages that have not engulfed a cancer cell. Yellow represent double positive macrophages that have ingested a cancer cell. (FIG. 5B) Phagocytosis of DLD1 parental, knockout, isoform 1, and isoform 2 lines. Data is normalized to DLD1 parental treated with IGG4 antibodies. (FIG. 5C) Phagocytosis of DLD1 parental, knockout, isoform 1, and isoform 2 lines sorted by cell type. Data is normalized to DLD1 parental treated with IGG4 antibodies. (FIG. 5D) Phagocytosis of SW620 parental, knockout, isoform 1, and isoform 2 lines. Data is normalized to SW620 parental treated with IGG4 antibodies. (FIG. 5E) Phagocytosis of SW620 parental, knockout, isoform 1, and isoform 2 lines sorted by cell type. Data is normalized to SW620 parental treated with IGG4 antibodies.

(FIG. 6A) Phase-contrast microscopy of DLD1 at 40× magnification. (FIG. 6B) Confocal immunofluorescence microscopy of DLD1 at 40× magnification. Anti-KDEL Cy3 is shown in yellow and labels the ER and Golgi. Anti-CD47 AlexaFluor647 (clone B6H12) is shown in magenta and labels CD47 protein. DAPI is shown in blue in the overlay images and labels the nucleus.

(FIG. 7A) Tumor burden of NSG mice one week post-injection with DLD1 Isoform 1. (FIG. 7B) Caliper measurements of tumors of NSG mice engrafted with DLD1 Parental, Knockout, Isoform 1, or Isoform 2. Mice were treated with anti-CD47 antibodies (clone 5F9) or untreated (PBS control). (FIG. 7C) Caliper measurements of tumors of NSG mice engrafted with DLD1 Isoform 1 or Isoform 2. Mice were treated with anti-CD47 antibodies (clone 5F9) or untreated (PBS control). (FIG. 7D) Caliper measurements of tumors of NSG mice engrafted with DLD1 Isoform 1 or Isoform 2. Mice were treated with anti-CD47 antibodies (clone 5F9) or untreated (PBS control). (FIG. 7E) Kaplan-Meier survival plot comparing NSG mice carrying DLD1 Isoform 1 or Isoform 2 xenografts. Mice were treated with anti-CD47 antibodies (clone 5F9) or untreated (PBS control).

DETAILED DESCRIPTION OF THE INVENTION

Figure 1A:
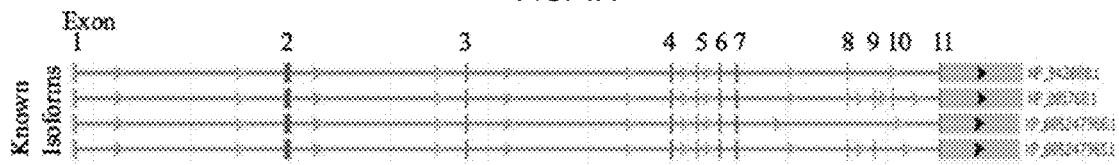
FIG. 1A-1E.

The present invention relates to methods of determining whether a cell or population of cells is responsive to an anti-CD47 agent and methods of determining whether an individual is maintaining responsiveness to an anti-CD47 agent, the methods comprising assaying biological samples for the level of at least CD47 isoform. The present invention further relates to kits for performing the methods.

Before the present methods and kits are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Biological Sample.

The term "sample" with respect to an individual encompasses blood and other liquid samples of biological origin, solid tissue samples such as a biopsy specimen or tissue cultures or cells derived or isolated therefrom and the progeny thereof. The definition also includes samples that have been manipulated in any way after their procurement, such as by treatment with reagents; washed; or enrichment for certain cell populations, such as cancer cells. The definition also includes samples that have been enriched for particular types of molecules, e.g., nucleic acids, polypeptides, etc.

The term "biological sample" encompasses a clinical sample. The types of "biological samples" include, but are not limited to: tissue obtained by surgical resection, tissue obtained by biopsy, cells in culture, cell supernatants, cell lysates, tissue samples, organs, bone marrow, blood, plasma, serum, fine needle aspirate, lymph node aspirate, cystic aspirate, a paracentesis sample, a thoracentesis sample, and the like. A "biological sample" can include cells (e.g., target cells, normal cells, blood cells, tissue cells etc.) can be suspected of comprising such cells, or can be devoid of cells. A biological sample can include biological fluids derived from cells (e.g., a cancerous cell, an infected cell, etc.), e.g., a sample comprising polynucleotides and/or polypeptides that is obtained from such cells (e.g., a cell lysate or other cell extract comprising polynucleotides and/or polypeptides). A biological sample comprising an inflicted cell from a patient can also include non-inflicted cells. In some embodiments the biological sample is blood or a derivative thereof, e.g. plasma, serum, etc.

Obtaining and Assaying a Sample.

The term "assaying" is used herein to include the physical steps of manipulating a biological sample to generate data related to the sample. As will be readily understood by one of ordinary skill in the art, a biological sample must be "obtained" prior to assaying the sample. Thus, the term "assaying" implies that the sample has been obtained. The terms "obtained" or "obtaining" as used herein encompass the act of receiving an extracted or isolated biological sample. For example, a testing facility can "obtain" a biological sample in the mail (or via delivery, etc.) prior to assaying the sample. In some such cases, the biological sample was "extracted" or "isolated" from an individual by another party prior to mailing (i.e., delivery, transfer, etc.), and then "obtained" by the testing facility upon arrival of the sample. Thus, a testing facility can obtain the sample and then assay the sample, thereby producing data related to the sample.

The terms "obtained" or "obtaining" as used herein can also include the physical extraction or isolation of a biological sample from a subject. Accordingly, a biological sample can be isolated from a subject (and thus "obtained") by the same person or same entity that subsequently assays the sample. When a biological sample is "extracted" or "isolated" from a first party or entity and then transferred (e.g., delivered, mailed, etc.) to a second party, the sample was "obtained" by the first party (and also "isolated" by the first party), and then subsequently "obtained" (but not "isolated") by the second party. Accordingly, in some embodiments, the step of obtaining does not comprise the step of isolating a biological sample.

In some embodiments, the step of obtaining comprises the step of isolating a biological sample (e.g., a pre-treatment biological sample, a post-treatment biological sample, etc.). Methods and protocols for isolating various biological samples (e.g., a blood sample, a serum sample, a plasma sample, a biopsy sample, an aspirate, etc.) will be known to one of ordinary skill in the art and any convenient method may be used to isolate a biological sample.

It will be understood by one of ordinary skill in the art that in some cases, it is convenient to wait until multiple samples (e.g., a pre-treatment biological sample and a post-treatment biological sample) have been obtained prior to assaying the samples. Accordingly, in some cases an isolated biological sample (e.g., a pre-treatment biological sample, a post-treatment biological sample, etc.) is stored until all appropriate samples have been obtained. One of ordinary skill in the art will understand how to appropriately store a variety of different types of biological samples and any convenient method of storage may be used (e.g., refrigeration) that is appropriate for the particular biological sample. In some embodiments, a pre-treatment biological sample is assayed prior to obtaining a post-treatment biological sample. In some cases, a pre-treatment biological sample and a post-treatment biological sample are assayed in parallel. In some cases, multiple different post-treatment biological samples and/or a pre-treatment biological sample are assayed in parallel. In some cases, biological samples are processed immediately or as soon as possible after they are obtained.

In subject methods, the concentration (i.e., "level"), or expression level of a gene product, which may be an RNA, a protein, etc., in a biological sample is measured (i.e., "determined"). By "expression level" (or "level") it is meant the level of gene product (e.g. the absolute and/or normalized value determined for the RNA expression level of a CD47 isoform or for the expression level of the encoded polypeptide, or the concentration of the protein in a biological sample). The term "gene product" or "expression product" are used herein to refer to the RNA transcription products (RNA transcripts, e.g. mRNA, an unspliced RNA, a splice variant mRNA, and/or a fragmented RNA) of the gene, including mRNA, and the polypeptide translation products of such RNA transcripts. A gene product can be, for example, an unspliced RNA, an mRNA, a splice variant mRNA, a microRNA, a fragmented RNA, a polypeptide, a post-translationally modified polypeptide, a splice variant polypeptide, etc.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assaying may be relative or absolute. For example, "assaying" can be determining whether the expression level is less than or "greater than or equal to" a particular threshold, (the threshold can be pre-determined or can be determined by assaying a control sample). On the other hand, "assaying to determine the expression level" can mean determining a quantitative value (using any convenient metric) that represents the level of expression (i.e., expression level, e.g., the amount of protein and/or RNA, e.g., mRNA) of a particular CD47 isoform. The level of expression can be expressed in arbitrary units associated with a particular assay (e.g., fluorescence units, e.g., mean fluorescence intensity (MFI)), or can be expressed as an absolute value with defined units (e.g., number of mRNA transcripts, number of protein molecules, concentration of protein, etc.). Additionally, the level of expression of a CD47 isoform can be compared to the expression level of one or more additional genes (e.g., nucleic acids and/or their encoded proteins) to derive a normalized value that represents a normalized expression level. The specific metric (or units) chosen is not crucial as long as the same units are used (or conversion to the same units is performed) when evaluating multiple biological samples from the same individual (e.g., biological samples taken at different points in time from the same individual). This is because the units cancel when calculating a fold-change (i.e., determining a ratio) in the expression level from one biological sample to the next (e.g., biological samples taken at different points in time from the same individual).

For measuring RNA levels, the amount or level of an RNA in the sample is determined. In some instances, the expression level of one or more additional RNAs may also be measured, and the level of CD47 isoform expression compared to the level of the one or more additional RNAs to provide a normalized value for the CD47 isoform expression level. Any convenient protocol for evaluating RNA levels may be employed wherein the level of one or more RNAs in the assayed sample is determined.

A number of exemplary methods for measuring RNA (e.g., mRNA) expression levels (e.g., expression level of a nucleic acid CD47 isoform) in a sample are known by one of ordinary skill in the art, and any convenient method can be used. Exemplary methods include, but are not limited to: hybridization-based methods (e.g., Northern blotting, array hybridization (e.g., microarray); in situ hybridization; in situ hybridization followed by FACS; and the like)(Parker & Barnes, Methods in Molecular Biology 106:247-283 (1999)); RNAse protection assays (Hod, Biotechniques 13:852-854 (1992)); PCR-based methods (e.g., reverse transcription PCR (RT-PCR), quantitative RT-PCR (qRT-PCR), real-time RT-PCR, etc.) (Weis et al., Trends in Genetics 8:263-264 (1992)); nucleic acid sequencing methods (e.g., Sanger sequencing, Next Generation sequencing (i.e., massive parallel high throughput sequencing, e.g., Illumina's reversible terminator method, Roche's pyrosequencing method (454), Life Technologies' sequencing by ligation (the SOLID platform), Life Technologies' Ion Torrent platform, single molecule sequencing, etc.); and the like.

In some embodiments, the biological sample can be assayed directly. In some embodiments, nucleic acid of the biological sample is amplified (e.g., by PCR) prior to assaying. As such, techniques such as PCR (Polymerase Chain Reaction), RT-PCR (reverse transcriptase PCR), qRT-PCR (quantitative RT-PCR, real time RT-PCR), etc. can be used prior to the hybridization methods and/or the sequencing methods discussed above.

For measuring mRNA levels, the starting material is typically total RNA or poly A+RNA isolated from a biological sample (e.g., suspension of cells from a peripheral blood sample, a bone marrow sample, etc., or from a homogenized tissue, e.g. a homogenized biopsy sample, an aspirate, a homogenized paraffin- or OCT-embedded sample, etc.). General methods for mRNA extraction are well known in the art and are disclosed in standard textbooks of molecular biology, including Ausubel et al., Current Protocols of Molecular Biology, John Wiley and Sons (1997). RNA isolation can also be performed using a purification kit, buffer set and protease from commercial manufacturers, according to the manufacturer's instructions. For example, RNA from cell suspensions can be isolated using Qiagen RNeasy mini-columns, and RNA from cell suspensions or homogenized tissue samples can be isolated using the TRIzol reagent-based kits (Invitrogen), MasterPure™ Complete DNA and RNA Purification Kit (EPICENTRE™, Madison, Wis.), Paraffin Block RNA Isolation Kit (Ambion, Inc.) or RNA Stat-60 kit (Tel-Test).

A variety of different manners of measuring mRNA levels are known in the art, e.g. as employed in the field of differential gene expression analysis. One representative and convenient type of protocol for measuring mRNA levels is array-based gene expression profiling. Such protocols are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively.

Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions, and unbound nucleic acid is then removed. The term "stringent assay conditions"

as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

The resultant pattern of hybridized nucleic acid provides information regarding expression for each of the genes that have been probed, where the expression information is in terms of whether or not the gene is expressed and, typically, at what level, where the expression data, i.e., expression profile (e.g., in the form of a transcriptosome), may be both qualitative and quantitative.

Alternatively, non-array based methods for quantitating the level of one or more nucleic acids in a sample may be employed. These include those based on amplification protocols, e.g., Polymerase Chain Reaction (PCR)-based assays, including quantitative PCR, reverse-transcription PCR (RT-PCR), real-time PCR, and the like, e.g. TaqMan® RT-PCR, MassARRAY® System, BeadArray® technology, and Luminex technology; and those that rely upon hybridization of probes to filters, e.g. Northern blotting and in situ hybridization.

Examples of some of the nucleic acid sequencing methods listed above are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps.

For measuring protein levels, the amount or level of a polypeptide in the biological sample is determined. In some embodiments concentration is a relative value measured by comparing the level of one protein relative to another protein. In other embodiments the concentration is an absolute measurement of weight/volume or weight/weight.

In some cases, the cells are removed from the biological sample (e.g., via centrifugation, via adhering cells to a dish or to plastic, etc.) prior to measuring the concentration. In some cases, the intracellular protein level is measured by lysing the removed cells of the biological sample to measure the level of protein in the cellular contents. In some cases, both the extracellular and intracellular levels of protein are measured by separating the cellular and fluid portions of the biological sample (e.g., via centrifugation), measuring the extracellular level of the protein by measuring the level of protein in the fluid portion of the biological sample, and measuring the intracellular level of protein by measuring the level of protein in the cellular portion of the biological sample (e.g., after lysing the cells). In some cases, the total level of protein (i.e., combined extracellular and intracellular protein) is measured by lysing the cells of the biological sample to include the intracellular contents as part of the sample.

In some instances, the concentration of one or more additional proteins may also be measured, and CD47 isoform concentration compared to the level of the one or more additional proteins to provide a normalized value for the CD47 isoform concentration. Any convenient protocol for evaluating protein levels may be employed wherein the level of one or more proteins in the assayed sample is determined.

While a variety of different manners of assaying for protein levels are known to one of ordinary skill in the art and any convenient method may be used, one representative and convenient type of protocol for assaying protein levels is ELISA, an antibody-based method. In ELISA and ELISA-based assays, one or more antibodies specific for the proteins of interest may be immobilized onto a selected solid surface, preferably a surface exhibiting a protein affinity such as the wells of a polystyrene microtiter plate. After washing to remove incompletely adsorbed material, the assay plate wells are coated with a non-specific "blocking" protein that is known to be antigenically neutral with regard to the test sample such as bovine serum albumin (BSA), casein or solutions of powdered milk. This allows for blocking of non-specific adsorption sites on the immobilizing surface, thereby reducing the background caused by non-specific binding of antigen onto the surface. After washing to remove unbound blocking protein, the immobilizing surface is contacted with the sample to be tested under conditions that are conducive to immune complex (antigen/antibody) formation. Following incubation, the antisera-contacted surface is washed so as to remove non-immunocomplexed material. The occurrence and amount of immunocomplex formation may then be determined by subjecting the bound immunocomplexes to a second antibody having specificity for the target that differs from the first antibody and detecting binding of the second antibody. In certain embodiments, the second antibody will have an associated enzyme, e.g. urease, peroxidase, or alkaline phosphatase, which will generate a color precipitate upon incubating with an appropriate chromogenic substrate. After such incubation with the second antibody and washing to remove unbound material, the amount of label is quantified, for example by incubation with a chromogenic substrate such as urea and bromocresol purple in the case of a urease label or 2,2'-azino-di-(3-ethyl-benzothiazoline)-6-sulfonic acid (ABTS) and H2O2, in the case of a peroxidase label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody. The solid substrate upon which the antibody or antibodies are immobilized can be made of a wide variety of materials and in a wide variety of shapes, e.g., microtiter plate, microbead, dipstick, resin particle, etc. The substrate may be chosen to maximize signal to noise ratios, to minimize background binding, as well as for ease of separation and cost. Washes may be effected in a manner most appropriate for the substrate being used, for example, by removing a bead or dipstick from a reservoir, emptying or diluting a reservoir such as a microtiter plate well, or rinsing a bead, particle, chromatographic column or filter with a wash solution or solvent.

Alternatively, non-ELISA based-methods for measuring the levels of one or more proteins in a sample may be employed. Representative exemplary methods include but are not limited to antibody-based methods (e.g., Western blotting, proteomic arrays, xMAP™ microsphere technology (e.g., Luminex technology), immunohistochemistry, flow cytometry, and the like) as well as non antibody-based methods (e.g., mass spectrometry).

Anti-CD47 Agent.

As used herein, the term "anti-CD47 agent" or "CD47-blocking agent" refers to any agent that reduces the binding of CD47 (e.g., on a target cell) to SIRPα (e.g., on a phagocytic cell). Non-limiting examples of suitable anti-CD47 reagents include SIRPα reagents, including without limitation high affinity SIRPα polypeptides, anti-SIRPα, antibodies, soluble CD47 polypeptides, and anti-CD47 antibodies or antibody fragments. In some embodiments, a suitable anti-CD47 agent (e.g. an anti-CD47 antibody, a SIRPα reagent, etc.) specifically binds CD47 to reduce the binding of CD47 to SIRPα.

In some embodiments, a suitable anti-CD47 agent (e.g., an anti-SIRPα, antibody, a soluble CD47 polypeptide, etc.) specifically binds SIRPα to reduce the binding of CD47 to SIRPα. A suitable anti-CD47 agent that binds SIRPα does not activate SIRPα (e.g., in the SIRPα-expressing phagocytic cell). The efficacy of a suitable anti-CD47 agent can be assessed by assaying the agent (further described below). In an exemplary assay, target cells are incubated in the presence or absence of the candidate agent. An agent for use in the methods of the invention will up-regulate phagocytosis by at least 5% (e.g., at least 10%, at least 20%, at least 30%, at least 40%, at least 50%, at least 60%, at least 70%, at least 80%, at least 90%, at least 100%, at least 120%, at least 140%, at least 160%, at least 180%, at least 200%, at least 500%, at least 1000%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47 agent does not activate CD47 upon binding. When CD47 is activated, a process akin to apoptosis (i.e., programmed cell death) may occur (Manna and Frazier, Cancer Research, 64, 1026-1036, Feb. 1, 2004). Thus, in some embodiments, the anti-CD47 agent does not directly induce cell death of a CD47-expressing cell.

SIRPα Reagent.

A SIRPα reagent comprises the portion of SIRPα that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. The SIRPα reagent will usually comprise at least the d1 domain of SIRPα. In some embodiments, a SIRPα reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules.

In some embodiments, a subject anti-CD47 agent is a "high affinity SIRPα reagent", which includes SIRPα-derived polypeptides and analogs thereof (e.g., CV1-hIgG4). High affinity SIRPα reagents are described in international application PCT/US13/21937, which is hereby specifically incorporated by reference. High affinity SIRPα reagents are variants of the native SIRPα protein. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

A high affinity SIRPα reagent comprises the portion of SIRPα that is sufficient to bind CD47 at a recognizable affinity, e.g., high affinity, which normally lies between the signal sequence and the transmembrane domain, or a fragment thereof that retains the binding activity. The high affinity SIRPα reagent will usually comprise at least the d1 domain of SIRPα with modified amino acid residues to increase affinity. In some embodiments, a SIRPα variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc.

Anti-CD47 Antibodies.

In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Some anti-CD47 antibodies do not reduce the binding of CD47 to SIRPα (and are therefore not considered to be an "anti-CD47 agent" herein) and such an antibody can be referred to as a "non-blocking anti-CD47 antibody." A suitable anti-CD47 antibody that is an "anti-CD47 agent" can be referred to as a "CD47-blocking antibody". A non-limiting example of a non-blocking antibody is anti-CD47 antibody 2D3, which binds to CD47, but does not reduce the interaction between CD47 and SIRPα. Non-limiting examples of suitable antibodies include clones B6H12, 5F9, 8B6, and C3 (for example as described in International Patent Publication WO 2011/143624, herein specifically incorporated by reference). Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Anti-SIRPα Antibodies.

In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of inflicted cells over normal cells. Those cells that express higher levels of CD47 (e.g., infected cells) relative to other cells (non-infected cells) will be preferentially phagocytosed. Thus, a suitable anti-SIRPα antibody specifically binds SIRPα (without activating/ stimulating enough of a signaling response to inhibit phagocytosis) and blocks an interaction between SIRPα and CD47. Suitable anti-SIRPα antibodies include fully human, humanized or chimeric versions of such antibodies. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Soluble CD47 Polypeptides.

In some embodiments, a subject anti-CD47 agent is a soluble CD47 polypeptide that specifically binds SIRPα and reduces the interaction between CD47 on one cell (e.g., an infected cell) and SIRPα on another cell (e.g., a phagocytic cell). A suitable soluble CD47 polypeptide can bind SIRPα without activating or stimulating signaling through SIRPα because activation of SIRPα would inhibit phagocytosis. Instead, suitable soluble CD47 polypeptides facilitate the preferential phagocytosis of infected cells over non-infected cells. Those cells that express higher levels of CD47 (e.g., infected cells) relative to normal, non-target cells (normal cells) will be preferentially phagocytosed. Thus, a suitable soluble CD47 polypeptide specifically binds SIRPα without activating/stimulating enough of a signaling response to inhibit phagocytosis.

In some cases, a suitable soluble CD47 polypeptide can be a fusion protein (for example as structurally described in US Patent Publication US20100239579, herein specifically incorporated by reference). However, only fusion proteins that do not activate/stimulate SIRPα are suitable for the methods provided herein. Suitable soluble CD47 polypeptides also include any peptide or peptide fragment comprising variant or naturally existing CD47 sequences (e.g., extracellular domain sequences or extracellular domain variants) that can specifically bind SIRPα and inhibit the interaction between CD47 and SIRPα without stimulating enough SIRPα activity to inhibit phagocytosis.

In certain embodiments, soluble CD47 polypeptide comprises the extracellular domain of CD47, including the signal peptide, such that the extracellular portion of CD47 is typically 142 amino acids in length, and has the amino acid sequence set forth in, for example, the Genbank reference sequence for human CD47, including NP_942088 or NP_001768.1. The soluble CD47 polypeptides described herein also include CD47 extracellular domain variants that comprise an amino acid sequence at least 65%-75%, 75%-80%, 80-85%, 85%-90%, or 95%-99% (or any percent identity not specifically enumerated between 65% to 100%), which variants retain the capability to bind to SIRPα without stimulating SIRPα signaling.

In certain embodiments, the signal peptide amino acid sequence may be substituted with a signal peptide amino acid sequence that is derived from another polypeptide (e.g., for example, an immunoglobulin or CTLA4). For example, unlike full-length CD47, which is a cell surface polypeptide that traverses the outer cell membrane, the soluble CD47 polypeptides are secreted; accordingly, a polynucleotide encoding a soluble CD47 polypeptide may include a nucleotide sequence encoding a signal peptide that is associated with a polypeptide that is normally secreted from a cell.

In other embodiments, the soluble CD47 polypeptide comprises an extracellular domain of CD47 that lacks the signal peptide (124 amino acids). As described herein, signal peptides are not exposed on the cell surface of a secreted or transmembrane protein because either the signal peptide is cleaved during translocation of the protein or the signal peptide remains anchored in the outer cell membrane (such a peptide is also called a signal anchor). The signal peptide sequence of CD47 is believed to be cleaved from the precursor CD47 polypeptide in vivo.

In other embodiments, a soluble CD47 polypeptide comprises a CD47 extracellular domain variant. Such a soluble CD47 polypeptide retains the capability to bind to SIRPα without stimulating SIRPα signaling. The CD47 extracellular domain variant may have an amino acid sequence that is at least 65%-75%, 75%-80%, 80-85%, 85%-90%, or 95%-99% identical (which includes any percent identity between any one of the described ranges) to a reference human CD47 sequence.

Additional Terms.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer, those with an infection, etc.) as well as those in which prevention is desired (e.g., those with increased susceptibility to cancer, those suspected of having cancer, etc.).

A target cell can have cancer, can harbor an infection (e.g., a chronic infection), and other hyper-proliferative conditions, for example sclerosis, fibrosis, and the like, etc. "Inflicted cells" may be those cells that cause the symptoms, illness, or disease. As non-limiting examples, the inflicted cells of a patient can be cancer cells, infected cells, and the like. One indication that an illness or disease can be treated with an anti-CD47 agent is that the involved cells express an increased level of CD47 isoform 1 compared to normal cells of the same cell type.

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

Examples of symptoms, illnesses, and/or diseases that can be treated with an anti-CD47 agent include, but are not limited to cancer and infection (e.g., chronic infection). As used herein "cancer" includes any form of cancer (e.g., leukemia; acute myeloid leukemia (AML); acute lymphoblastic leukemia (ALL); metastasis; minimal residual disease; solid tumor cancers, e.g., lung, prostate, breast, bladder, colon, ovarian, glioblastoma, medulloblastoma, leiomyosarcoma, and head & neck squamous cell carcinomas, melanomas; etc.). Any cancer, where the cancer cells exhibit increased expression of CD47 or pro-phagocytic "eat me" signals compared to non-cancer cells, is a suitable cancer to be treated by the subject methods and kits.

As used herein, the term "infection" refers to any state in at least one cell of an organism (i.e., a subject) is infected by an infectious agent (e.g., a subject has an intracellular pathogen infection, e.g., a chronic intracellular pathogen infection). As used herein, the term "infectious agent" refers to a foreign biological entity (i.e. a pathogen) that induces increased CD47 expression or upregulation of pro-phagocytic "eat me" signals in at least one cell of the infected organism. For example, infectious agents include, but are not limited to bacteria, viruses, protozoans, and fungi. Intracellular pathogens are of particular interest. Infectious diseases are disorders caused by infectious agents. Some infectious agents cause no recognizable symptoms or disease under certain conditions, but have the potential to cause symptoms or disease under changed conditions. The subject methods can be used in the treatment of chronic pathogen infections, for example including but not limited to viral infections, e.g. retrovirus, lentivirus, hepadna virus, herpes viruses, pox viruses, human papilloma viruses, etc.; intracellular bacterial infections, e.g. *Mycobacterium, Chlamydophila, Ehrlichia, Rickettsia, Brucella, Legionella, Francisella, Listeria, Coxiella, Neisseria, Salmonella, Yersinia* sp, *Helicobacter pylori* etc.; and intracellular protozoan pathogens, e.g. *Plasmodium* sp, *Trypanosoma* sp., *Giardia* sp., *Toxoplasma* sp., *Leishmania* sp., etc.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

A "therapeutically effective dose" or "therapeutic dose" is an amount sufficient to effect desired clinical results (i.e., achieve therapeutic efficacy). A therapeutically effective dose can be administered in one or more administrations. For purposes of this invention, a therapeutically effective dose of an anti-CD47 agent is an amount that is sufficient to palliate, ameliorate, stabilize, reverse, prevent, slow or delay the progression of the disease state (e.g., cancer or chronic infection) by increasing phagocytosis of a target cell (e.g., a target cell). Thus, a therapeutically effective dose of an anti-CD47 agent reduces the binding of CD47 on a target cell, to SIRPα on a phagocytic cell, at an effective dose for increasing the phagocytosis of the target cell.

In some embodiments, a therapeutically effective dose is one that provides for sustained serum levels of anti-CD47 agent (e.g., an anti-CD47 antibody) of about 40 µg/ml or more (e.g, about 50 ug/ml or more, about 60 ug/ml or more, about 75 ug/ml or more, about 100 ug/ml or more, about 125 ug/ml or more, or about 150 ug/ml or more). In some embodiments, a therapeutically effective dose leads to sustained serum levels of anti-CD47 agent (e.g., an anti-CD47 antibody) that range from about 40 µg/ml to about 300 ug/ml (e.g, from about 40 ug/ml to about 250 ug/ml, from about 40 ug/ml to about 200 ug/ml, from about 40 ug/ml to about 150 ug/ml, from about 40 ug/ml to about 100 ug/ml, from about 50 ug/ml to about 300 ug/ml, from about 50 ug/ml to about 250 ug/ml, from about 50 ug/ml to about 200 ug/ml, from about 50 ug/ml to about 150 ug/ml, from about 75 ug/ml to about 300 ug/ml from about 75 ug/ml to about 250 ug/ml, from about 75 ug/ml to about 200 ug/ml, from about 75 ug/ml to about 150 ug/ml, from about 100 ug/ml to about 300 ug/ml, from about 100 ug/ml to about 250 ug/ml, or from about 100 ug/ml to about 200 ug/ml). In some embodiments, a therapeutically effective dose for treating solid tumors provides for sustained serum levels of anti-CD47 agent (e.g., an anti-CD47 antibody) of about 100 µg/ml or more (e.g., sustained serum levels that range from about 100 ug/ml to about 200 ug/ml). In some embodiments, a therapeutically effective dose for treating non-solid tumors (e.g., acute myeloid leukemia (AML)) provides for sustained serum levels of anti-CD47 agent (e.g., an anti-CD47 antibody) of about 50 µg/ml or more (e.g., sustained serum levels of 75 µg/ml or more; or sustained serum levels that range from about 50 ug/ml to about 150 ug/ml).

Accordingly, a single therapeutically effective dose or a series of therapeutically effective doses would be able to achieve and maintain a serum level of anti-CD47 agent. A therapeutically effective dose of an anti-CD47 agent can depend on the specific agent used, but is usually about 2 mg/kg body weight or more (e.g., about 2 mg/kg or more, about 4 mg/kg or more, about 8 mg/kg or more, about 10 mg/kg or more, about 15 mg/kg or more, about 20 mg/kg or more, about 25 mg/kg or more, about 30 mg/kg or more, about 35 mg/kg or more, or about 40 mg/kg or more), or from about 10 mg/kg to about 40 mg/kg (e.g., from about 10 mg/kg to about 35 mg/kg, or from about 10 mg/kg to about 30 mg/kg). The dose required to achieve and/or maintain a particular serum level is proportional to the amount of time between doses and inversely proportional to the number of doses administered. Thus, as the frequency of dosing increases, the required dose decreases. The optimization of dosing strategies will be readily understood and practiced by one of ordinary skill in the art.

A sub-therapeutic dose is a dose (i.e., an amount) that is not sufficient to effect the desired clinical results. For example, a sub-therapeutic dose of an anti-CD47 agent is an amount that is not sufficient to palliate, ameliorate, stabilize, reverse, prevent, slow or delay the progression of the disease state (e.g., cancer, infection, inflammation, etc.). In some cases, it is desirable to use a sub-therapeutic dose of an anti-CD47 agent as a primer agent (described in more detail below). While the use of a sub-therapeutic dose of an anti-CD47 agent as a primer agent achieves a desired outcome (e.g., the subject is "primed" to receive a therapeutically effective dose), the dose is not considered to be a "therapeutic dose" because the sub-therapeutic dose does not effectively increase phagocytosis of a target cell and is not sufficient to palliate, ameliorate, stabilize, reverse, prevent, slow or delay the progression of the disease state. A sub-therapeutic dose of an anti-CD47 agent can depend on the specific agent used, but is generally less than about 10 mg/kg.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides, or binding of a SIRPα polypeptide). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member). Suitable specific binding members include agents that specifically bind CD47 and/or SIRPα (i.e., anti-CD47 agents), or that otherwise block the interaction between CD47 and SIRPα.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The terms "phagocytic cells" and "phagocytes" are used interchangeably herein to refer to a cell that is capable of phagocytosis. There are three main categories of phagocytes: macrophages and mononuclear cells (histiocytes and monocytes); polymorphonuclear leukocytes (neutrophils); and dendritic cells.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

"Providing an analysis" is used herein to refer to the delivery of an oral or written analysis (i.e., a document, a report, etc.). A written analysis can be a printed or electronic document. A suitable analysis (e.g., an oral or written report) provides any or all of the following information: identifying information of the subject (name, age, etc.), a description of what type of biological sample(s) was used and/or how it was used, the technique used to assay the sample, the results of the assay, the assessment as to whether the individual is determined to be responsive or not responsive to the anti-CD47 agent, a recommendation to continue or alter therapy, a recommended strategy for additional therapy, etc. The report can be in any format including, but not limited to printed information on a suitable medium or substrate (e.g., paper); or electronic format. If in electronic format, the report can be in any computer readable medium, e.g., diskette, compact disk (CD), flash drive, and the like, on which the information has been recorded. In addition, the report may be present as a website address which may be used via the internet to access the information at a remote site.

Methods

Methods are provided for determining whether a cell or cell population is responsive to an anti-CD47 agent and for determining prognosis for aggressiveness of a cancer. The subject methods include a step of assaying a biological sample comprising the cell or cells of interest to determine the level or ratio of CD47 isoforms. If a ratio is determined, a cell is considered to be a predominantly CD47 isoform 1 type if the ratio of isoform 1 to other CD47 isoforms is at least 1:5, at least 1:3, at least 1:2, at least 1:1, at least 2:1, at least 3:1, at least 5:1, at least 7:1, at least 10:1 or more.

The level or ratio of isoforms in a pre-treatment biological sample can be referred to as a "pre-treatment value" because the first biological sample is isolated from the individual prior to the administration of an anti-CD47 agent (i.e., "pre-treatment"). The level or ratio of isoforms in a pre-treatment biological sample can also be referred to as a "baseline value". In some cases, the baseline value is determined by determining the level or ratio of isoforms from multiple (i.e., more than one, e.g., two or more, three or more, for or more, five or more, etc.) pre-treatment biological samples. In some cases, the multiple pre-treatment biological samples are isolated from an individual at different time points in order to assess natural fluctuations in expression levels prior to treatment. In some embodiments, all of the pre-treatment biological samples will be the same type of biological sample (e.g., a blood sample, a serum sample, a plasma sample, a biopsy sample, an aspirate, etc.). In some cases, two or more pre-treatment biological samples are pooled prior to determining the level or ratio of isoforms. In some cases, the level or ratio of isoforms is determined separately for two or more pre-treatment biological samples and a "pre-treatment value" is calculated by averaging the separate measurements.

In some cases, combinations of biomarkers are used in the subject methods, where the determination of a CD47 isoform level or ratio is combined with determination of other clinically relevant biomarkers, as appropriate for the specific cell of interest.

The term "responsive" as used herein means that the anti-CD47 agent is having the desired effect and the individual's body is responding appropriately to the administration of the anti-CD47 agent. For example, and not to bound by theory, the administration of an anti-CD47 agent is expected to block the interaction between CD47 on a target cell and SIRPα on a phagocytic cell (e.g., macrophage). When this blockage is successful, the body responds in multiple ways, one of which includes the activation of phagocytic cells, which (i) no longer receive "don't eat me" signals from the target cell, (ii) begin to actively phagocytose the target cell.

The determination that an individual will be responsive to an anti-CD47 agent is a direct and active clinical application of the correlation between CD47 isoform expression and the activity of an anti-CD47 agent. For example, "determining" requires the active step of reviewing the data, which is produced during the active assaying step(s), and resolving whether an individual is or is not responsive (or maintaining responsiveness). Additionally, in some cases, a decision is made to proceed with the current treatment (i.e., therapy), or instead to alter the treatment. In some cases, the subject methods include the step of continuing therapy or altering therapy.

The term "continue treatment" (i.e., continue therapy) is used herein to mean that the current course of treatment (e.g., continued administration of an anti-CD47 agent) is to continue. For example, if the current course of treatment includes the administration of an anti-CD47 agent at a particular dose and/or with a particular dosing frequency (e.g., once per day, once every other day, etc.), than to "continue therapy" would be to continue administering the anti-CD47 agent at that particular dose and/or with that particular dosing frequency. If the current course of treatment includes a ramping (e.g., decreasing dose and/or frequency over time) of administration of an anti-CD47 agent, then "continue therapy" would mean to continue the ramping (e.g., until the individual is deemed to be non-responsive, at which point the therapy may be altered, e.g., the altered therapy may include an increased dose and/or frequency of an anti-CD47 agent).

Alternatively, "altering therapy" is used herein to mean "discontinuing therapy" or "changing the therapy" (e.g., changing the particular dose and/or frequency of anti-CD47 agent administration, e.g., increasing the dose and/or frequency). In some cases, therapy can be altered, e.g., increased, until a dose and/or frequency is reached at which the individual is deemed to be responsive. In some embodiments, altering therapy means changing which anti-CD47 agent is administered, discontinuing use of any anti-CD47 agent altogether, etc.

In some embodiments, determining whether an individual is responsive to an anti-CD47 agent comprises determining whether an individual exhibits a prolonged response to an anti-CD47 agent. In some such cases, an anti-CD47 agent is administered to the individual more than once (e.g., two or more times, three or more times, four or more times, five or more times, etc.). When administered more than once, an anti-CD47 agent can be administered at the same dose or at a different does than previously administered. A post-treatment biological sample can be isolated from an individual after any administration of an anti-CD47 agent. As a non-limiting example, in some cases, a pre-treatment biological sample is isolated from an individual (e.g., on day "0"); an anti-CD47 agent is administered more than once to the individual (e.g., on days "1", "3", "4", "6", and "9"); and a post-treatment biological sample is then isolated (e.g., after the fifth time an anti-CD47 agent is administered).

The anti-CD47 agent can be administered to an individual any time after a pre-treatment biological sample is isolated from the individual. The anti-CD47 agent may be administered simultaneous with or as soon as possible (e.g., about 7 days or less, about 3 days or less, e.g., 2 days or less, 36 hours or less, 1 day or less, 20 hours or less, 18 hours or less, 12 hours or less, 9 hours or less, 6 hours or less, 3 hours or less, 2.5 hours or less, 2 hours or less, 1.5 hours or less, 1 hour or less, 45 minutes or less, 30 minutes or less, 20 minutes or less, 15 minutes or less, 10 minutes or less, 5 minutes or less, 2 minutes or less, or 1 minute or less) after a pre-treatment biological sample is isolated (or, when multiple pre-treatment biological samples are isolated, after the final pre-treatment biological sample is isolated).

In some cases, a second anti-CD47 agent is administered to the individual. The second anti-CD47 agent can be the same agent and/or same dose as a previously administered anti-CD47 agent. In some cases, the anti-CD47 agent is a different agent and/or a different dose than a previously administered anti-CD47 agent. Any anti-CD47 agent can be administered one or more times as described above and any post-treatment biological sample can be isolated from the individual after any administration of an anti-CD47 agent. Thus, for example, after a first post-treatment biological sample is collected, an anti-CD47 agent can be administered to the individual one or more times and another post-treatment biological sample (e.g., a second, third, fourth, fifth, etc. post-treatment biological sample) can be isolated after any of the administrations of the anti-CD47 agent. When an anti-CD47 agent is administered to an individual more than once or when more than one anti-CD47 agent is administered, each administration of an anti-CD47 agent can take place in a range from about 2 hours to about 8 weeks (e.g., about 2 hours to about 48 hours, about 2 hours to about 36 hours, about 2 hours to about 24 hours, about 2 hours to about 12 hours, about 2 hours to about 6 hours, about 12 hours to about 4 weeks, about 12 hours to about 2 weeks, about 12 hours to about 1 week, about 12 hours to about 2 days, about 12 hours to about 36 hours, about 1 day to about 8 weeks, about 1 day to about 6 weeks, about 1 day to about 4 weeks, about 1 day to about 2 weeks, about 1 day to about 1 week, about 3 days to about 8 weeks, about 3 days to about 6 weeks, about 3 days to about 4 weeks, about 3 days to about 2 weeks, about 3 days to about 1 week, about 1 week to about 8 weeks, about 1 week to about 6 weeks, or about 1 week to about 4 weeks) after a previous administration of an anti-CD47 agent.

In some embodiments, the subject methods include providing an analysis indicating whether the individual is determined to be responsive or not responsive to the anti- CD47 agent, or whether the individual is determined to be maintaining responsiveness or not maintaining responsiveness to the anti-CD47 agent. As described above, an analysis can be an oral or written report (e.g., written or electronic document). The analysis can be provided to the subject, to the subject's physician, to a testing facility, etc. The analysis can also be accessible as a website address via the internet. In some such cases, the analysis can be accessible by multiple different entities (e.g., the subject, the subject's physician, a testing facility, etc.).

Administering an Anti-CD47 Agent.

Suitable anti-CD47 agents can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, the use of an anti-CD47 agent includes use in combination with another therapeutic agent (e.g., another anti-infection agent or another anti-cancer agent). Therapeutic formulations comprising one or more anti-CD47 agents of the invention are prepared for storage by mixing the anti-CD47 agent having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The anti-CD47 agent composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The anti-CD47 agent can be "administered" by any suitable means, including topical, oral, parenteral, intrapulmonary, and intranasal. Parenteral infusions include intramuscular, intravenous (bollus or slow drip), intraarterial, intraperitoneal, intrathecal or subcutaneous administration.

The anti-CD47 agent need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

An anti-CD47 agent is often administered as a pharmaceutical composition comprising an active therapeutic agent and another pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

A carrier may bear the agents in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear an anti-CD47 agent by non-covalent associations, such as non-covalent bonding or by encapsulation. The nature of the carrier can be either soluble or insoluble for purposes of the invention. Those skilled in the art will know of other suitable carriers for binding anti-CD47 agents, or will be able to ascertain such, using routine experimentation.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethyl-benzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Carriers and linkers specific for radionuclide agents include radiohalogenated small molecules and chelating compounds. A radionuclide chelate may be formed from chelating compounds that include those containing nitrogen and sulfur atoms as the donor atoms for binding the metal, or metal oxide, radionuclide.

Radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the methods of the invention. Such moieties may be conjugated to the anti-CD47 agent through an acceptable chemical linker or chelation carrier. Positron emitting moieties for use in the present invention include $^{18}F$, which can be easily conjugated by a fluorination reaction with the anti-CD47 agent.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the anti-CD47 agents can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in further optimizing a therapeutic dosage range for use in humans. The exact formulation, route of administration and dosage can be chosen by the individual physician in view of the patient's condition.

Suitable administration of an anti-CD47 agent (e.g., a therapeutically effective dose) can entail administration of a single dose, or can entail administration of doses daily, semi-weekly, weekly, once every two weeks, once a month, annually, etc. Dosage and frequency may vary depending on the half-life of the anti-CD47 agent in the patient. It will be understood by one of skill in the art that such guidelines will be adjusted for the molecular weight of the active agent, e.g. in the use of antibody fragments, in the use of antibody conjugates, in the use of SIRPα reagents, in the use of soluble CD47 peptides etc. The dosage may also be varied for localized administration, e.g. intranasal, inhalation, etc., or for systemic administration, e.g. i.m., i.p., i.v., and the like.

For more information on administering an anti-CD47 agent, see patent application U.S. Ser. No. 14/769,069 (Methods for Achieving Therapeutically Effective Doses of anti-CD47 Agents), which is hereby incorporated by reference in its entirety.

Kits

Also provided are kits for use in the methods. The subject kits include a tool (e.g., a PCR primer pair specific for a CD47 isoform, an antibody that specifically binds to a CD47 isoform, and the like) for determining the level of at least one isoform. The subject kits can also include an anti-CD47 agent. An anti-CD47 agent can be provided in a dosage form (e.g., a therapeutically effective dosage form). In some embodiments, an anti-CD47 agent is provided in two or more different dosage forms (e.g., two or more different therapeutically effective dosage forms). In the context of a kit, an anti-CD47 agent can be provided in liquid or solid form in any convenient packaging (e.g., stick pack, dose pack, etc.).

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

Utility

In some embodiments the cell is a cancer cell. A cancerous cell that expresses an increased level of CD47 isoform 1 relative to a non-cancerous cell of the same type can be treated with the subject methods.

The term "cancer", as used herein, refers to a variety of conditions caused by the abnormal, uncontrolled growth of cells. Cells capable of causing cancer, referred to as "cancer cells", possess characteristic properties such as uncontrolled proliferation, immortality, metastatic potential, rapid growth and proliferation rate, and/or certain typical morphological features. A cancer can be detected in any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer, and detecting a genotype indicative of a cancer. However, a negative result in one or more of the above detection methods does not necessarily indicate the absence of cancer, e.g., a patient who has exhibited a complete response to a cancer treatment may still have a cancer, as evidenced by a subsequent relapse.

The term "cancer" as used herein includes carcinomas, (e.g., carcinoma in situ, invasive carcinoma, metastatic carcinoma) and pre-malignant conditions, i.e. neomorphic changes independent of their histological origin. The term "cancer" is not limited to any stage, grade, histomorphological feature, invasiveness, aggressiveness or malignancy of an affected tissue or cell aggregation. In particular stage 0 cancer, stage I cancer, stage II cancer, stage III cancer, stage IV cancer, grade I cancer, grade II cancer, grade III cancer, malignant cancer and primary carcinomas are included.

Cancers and cancer cells that can be treated include, but are not limited to, hematological cancers, including leukemia, lymphoma and myeloma, and solid cancers, including for example tumors of the brain (glioblastomas, medulloblastoma, astrocytoma, oligodendroglioma, ependymomas), carcinomas, e.g. carcinoma of the lung, liver, thyroid, bone, adrenal, spleen, kidney, lymph node, small intestine, pancreas, colon, stomach, breast, endometrium, prostate, testicle, ovary, skin, head and neck, and esophagus.

In an embodiment, the cancer is a hematological cancer. In an embodiment, the hematological cancer is a leukemia. In another embodiment, the hematological cancer is a myeloma. In an embodiment, the hematological cancer is a lymphoma.

In an embodiment, the leukemia is selected from acute myeloid leukemia (AML), acute lymphocytic leukemia (ALL), chronic lymphocytic leukemia (CLL) and chronic myelogenous leukemia (CML). In an embodiment, the leukemia is AML. In an embodiment, the leukemia is ALL. In an embodiment, the leukemia is CLL. In a further embodiment, the leukemia is CML. In an embodiment, the cancer cell is a leukemic cell, for example, but not limited to, an AML cell, an ALL cell, a CLL cell or a CML cell.

Suitable cancers that can be responsive to treatment using an anti-CD47 agent include without limitation leukemia; acute myeloid leukemia (AML); acute lymphoblastic leukemia (ALL); metastasis; minimal residual disease; solid tumor cancers, e.g., breast, bladder, colon, ovarian, glioblastoma, leiomyosarcoma, and head & neck squamous cell carcinomas; etc. For examples, see: (i) Willingham et al., Proc Natl Acad Sci USA. 2012 Apr. 24; 109(17):6662-7: "The CD47-signal regulatory protein alpha (SIRPα) interaction is a therapeutic target for human solid tumors"; (ii) Edris et al., Proc Natl Acad Sci USA. 2012 Apr. 24; 109(17):6656-61: "Antibody therapy targeting the CD47 protein is effective in a model of aggressive metastatic leiomyosarcoma"; and (iii) US patent application 20110014119; all of which are herein incorporated in their entirety.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Functional Characterization of CD47 Splice-Variants

It is known that CD47 has at least four differently spliced mRNA variants with distinct tissue distributions. These four splice-variants differ from each other only at their intracytoplasmic carboxy termini, an important site for the initiation of internal cell signaling. Pre-mRNA splicing is a required step in the expression of most eukaryotic genes. Alternative splicing is the predominant way of generating multiple protein isoforms from individual genes, thereby expanding the repertoire of proteins in a cell. Each gene consists of multiple pieces (exons) that code for sections of a protein. Through alternative splicing, some exons are retained to produce the final protein while other exons are spliced out, thus producing different protein variants known as isoforms. These different isoforms may have similar, related, distinct, or antagonistic functions. Their expression may be controlled both spatially (different tissues and/or subcellular compartments) and temporally (different stages of development). Such tight regulation of isoform expression is crucial for maintaining homeostasis; failure may result in various developmental diseases and cancer.

Therefore, we hypothesized that not all isoforms of CD47 act as the "don't-eat-me" signal and the different isoforms may have distinct cell-specific functions. We further hypothesized that variations in the expression ratios of CD47 isoforms may confer a differential capacity on cancer cells to escape immune surveillance and may correlate with distinct tumor subtypes and patient outcomes. Different splice-variants may be selectively enriched in different cancers and may be directly responsible for conferring varying degrees of resistance to programmed cell removal. This is suggested by the observed synergy when cancer cells were treated with CD47-SIRPα interaction blocking antibodies (clones: HU5F9G4, B6H12) and other therapeutic antibodies to the same cancer.

Our lab has identified at least five different mRNA isoforms of CD47. The two most abundantly expressed isoforms are: isoform 1) the full-length splice-variant that has a cytoplasmic tail, and isoform 2) a shorter splice-variant that lacks the cytoplasmic tail. It was determined if the isoforms have redundant, related, or antagonistic functions that may be related or unrelated to CD47's role as the "don't-eat-me" signal. Determining the functions of different CD47 isoforms is crucial for developing targeted cancer therapy that effectively acts on the splice-variant that blocks the true "don't-eat-me" signal while minimizing the side effects that may result due to blocking other unknown functions of different CD47 isoforms.

The clinical trials of anti-CD47 antibody-mediated immunotherapy for various cancers are already underway. However, the functional implications of alternative splice-variants of CD47 remain unexplored. The results from this study can stratify cancer patients by identifying those who are most likely to benefit from the clinical trial of anti-CD47 antibodies. The distinct CD47 splice-variants can be biomarkers to predict patient outcome and response to the anti-CD47 antibody treatment. These biomarkers may be useful in identifying patients long before they develop advanced cancers based on their CD47 isoform composition, enabling physicians more time to recommend precautionary measures.

Materials and Methods

Tissue Culture. Multiple leukemia cancer cells from ATCC were purchased for screening: THF1, OCI AML, MV411, THP1 HL60, Kasumi-1, and MOLM3. Cells were cultured in RPMI with GlutaMAX media (Life Technologies) supplemented with 10% FBS and 1% PenStrep (Invitrogen) for 3 passages before DNA and RNA extraction. Cells were passaged using TrypLE Express Enzyme (Invitrogen) and cultured in 37 C with 5% $CO_2$ and 95% humidity.

DLD1 and SW620 colorectal cancer cells were also purchased from ATCC. DLD1 cells were cultured in RPMI with GlutaMAX media supplemented with 10% FBS and 1% PenStrep. SW620 cells were cultured in DMEM with GlutaMAX media (Life Technologies) supplemented with 10% FBS and 1% PenStrep. Cells were passaged using TrypLE Express Enzyme and cultured in 37 C with 5% $CO_2$ and 95% humidity.

RNA Extraction. Cell lines were propagated for at least 3 passages before RNA extraction. 10 million cells were lysed for RNA processing. RNA extraction was performed using TRIzol (Ambion) following the manufacturer's protocol. RNA was treated with RQ1 RNase-free DNase (Promega) and further purified with the RNeasy Plus Mini Kit from Qiagen. RNA was eluted in nuclease-free water and stored at −80 C.

Amplification and Sequencing of CD47 Splice-Variants. Primers targeting the CD47 gene were designed and purchased from ElimBio. The forward and reverse primers for extracted cDNA were (SEQ ID NO:1) 5'-GAGATGTGGC-CCCTGGTAG-3' and (SEQ ID NO:2) 5' GTTTGATG-GAAGCCACTGGT-3', respectively. The forward primer resides within exon 1 and the reverse primer resides within exon 11. The forward and reverse primers for extracted gDNA were (SEQ ID NO:3) 5'-TGAACAATGGAAATGT-TGCTG-3' and (SEQ ID NO:4) 5'-ATCACTTCACTTCA-GTTATTCATTAAGGGGTTCCTCTACA-3', respectively. The forward primer resides within intron 1 (between exon 1 and 2) and the reverse primer resides within exon 9-11.

Polymerase chain reaction (PCR) was performed using Phusion High-Fidelity PCR Master Mix with HF Buffer from NEB on the Veriti 96-Well Fast Thermal Cycler from ThermoFisher (Waltham, Mass.) under the following conditions: 95 C for 3 minutes, followed by 35 cycles of 95 C for 30 seconds, 60 C for 30 seconds, and 72 C for 60 seconds. The PCR products were run on 2% UltraPure Agarose (ThermoFisher) in 1×TBE. Band intensities for CD47 splice-variants were imaged with BioRad's Gel Doc XR+ System after staining with ethidium bromide (Sigma). The DNA bands corresponding to the specific CD47 splice-variants were excised from the agarose gel over an UV-lamp and purified with the MinElute Gel Extraction Kit from Qiagen. The gel-extracted DNA were verified by Sanger sequencing (ElimBio) using the same primers used to amplify them. Sequences were compared to known CD47 splice-variant sequences from NCBI's GenBank using the BLAST tool.

Cloning CD47 Splice-Variants in mammalian expression Plasmid Vectors. Empty pcDNA3.1 (+) vector was purchased from ThermoFisher. The complementary DNA (cDNA) containing the coding sequence (CDS) of CD47 Isoform 1 and Isoform 2 were purchased from commercial cDNA libraries (OpenBioSystems; Isoform 1: BC037306.1, Isoform 2: BC012884.1). The cDNA was amplified using the primers forward and reverse primers complementary to exon 1 and exon 11, respectively. The forward and reverse primers also included appropriate 5' linkers containing the palindromic BamHI and XbaI restriction endonuclease recognition sites, respectively. The cDNAs corresponding to the long (full-length isoform with the cytoplasmic tail) and the short (isoform without cytoplasmic tail) was amplified using PCR and the resulting amplicons were purified using PCR purification kit (Qiagen). The purified PCR products were digested using the BamHI (NEB) and XbaI (NEB), the DNA bands corresponding to the two CD47 cDNAs with staggered ends were resolved by agarose gel electrophoresis, excised and purified using gel purification kit from Qiagen. The empty pcDNA3.1 (+) vector was also digested by BamHI and XbaI, resolved on agarose gel, band corresponding to the linearized vector excised and purified using gel extraction kit in similar manner. The cDNA fragments with compatible end were ligated into the linearized pcDNA3.1 (+) vector between BamHI and XbaI restriction sites using T4 DNA ligase (NEB). The ligation reactions containing the ligated plasmid was used to transform StbI3 (Life Technologies) chemically competent E. coli cells by heat-shock method—briefly, ligated plasmid and chemically competent StbI3 cells were incubated on ice for 30 minutes followed by a 90 seconds of heat shock at 42° C. water bath followed by incubation on ice for 5 minutes. The transformed cells were allowed to recover for 1 hour at 37° C. after adding SOC media. Following recovery, the transformed StbI3 cells plated on LB+Ampicillin plates and incubated in a 37° C. incubator overnight. Next day 3-5 bacterial colonies with potential cloned pcDNA plasmid with the desired cDNA inserts were picked and were transferred to liquid culture in low-salt LB media with Ampicillin. After growth of bacterial cells, the plasmids were extracted from the cells with QIAprep Spin Miniprep Kit (Qiagen), verified that they contained the correct cDNA insert by Sanger sequencing (ElimBio).

DLD1 Transfection. DLD1 knockout target cells were passaged two days prior to transfection to achieve 40% confluency on the day of transfection. pcDNA vectors containing either CD47 Isoform 1 or Isoform 2 were transfected into DLD1-knockout cells using 293fectin Reagent from Invitrogen. Briefly, 3 µg of plasmid DNA were incubated for 30 minutes at room temperature with 10 µL of 293fectin reagent in 0.5 mL of OptiMEM media (Gibco). DLD1 target cells were incubated in serum-free media for 30 minutes prior to transfection. 500 µL of the transfection mix prepared above was added drop-by-drop to the target plate (10 cm dish) containing approximately 4 million cells (40% confluent). Cells were replenished with fresh media after 4 hours of incubation with the transfection mix.

Phagocytosis with anti-CD47 antibody treatment. To harvest human macrophages, leukocyte-rich samples of blood were obtained from the Stanford Blood Center from multiple blood donors. Blood samples were incubated for 30 minutes with CD14 microbeads (Miltenyi) and sorted for macrophages using a Miltenyi autoMACS machine with the preset Posselwb program. Collected peripheral blood mononuclear cells (PBMNCs) were counted and plated at a density of 10 million cells/plate in IMDM with GlutaMAX media (Life Technologies) supplemented with human AB serum (Corning) filtered through Nalgene Rapid-Flow 0.2 um PES filter units (Nalgene). Only the monocyte fraction (and possibly dendritic cells) adhere to the plates and survive after a day and all other cell-types die. The attached monocytes differentiate into macrophages after 7 days and can be lifted off of the plates and directly used for in vitro phagocytosis assay between 7-10 days after plating.

DLD1 cancer lines (parental, knockout, isoform 1, and isoform 2) grown in T-75 flasks as described above were trypsinized to get single cell suspension and stained at 1 ng/uL with anti-CD47 blocking antibodies—clones B6H12 & hu5F9G4—and non-blocking antibody, clone 2D3. Other treatment conditions included the Ig-like domain fragments of SIRPα that is most-distal to the plasma membrane, called (CV1), its dimer (MB), the CV1-dimer fused to a human IgG4 Fc domain called CV1G4, and an antibody against SIRPα (KWAR). As a control treatment with human IGG4 domain and cetuximab, which is an anti-epidermal growth factor receptor (EGFR) antibody, was also included. In addition, to single-agent treatment all possible dual-agent combination treatment was also tested. 100,000 of each of the parental or the engineered cancer cells (KO, ISO-1, or ISO-2 overexpressing cells) labelled with a green colored dye (Calcein-AM, ThermoFisher) were incubated in triplicates for each treatment condition in Corning Costar Ultra-Low attachment 96-well plates and co-incubated at 37° C. for two hours with 50,000 macrophages. Level of phagocytosis was analyzed flow cytometry using a BD LSRFortessa machine. Prior to flow cytometric analysis the macrophage-cancer cell mix was stained with APC-conjugated (red) anti-human CD45 antibody, which labels only the macrophages and they are derived from the peripheral blood monocytes. Therefore, after engulfing the green cancer cells, the macrophages that are eaters appear as a double-positive (red+green) population whereas the non-eaters appear as single positive (red) population. Phagocytic activity was defined as the percentage of double-positive macrophages compared to the total macrophage count.

Creating CD47-knockout lines. CD47 knockout lines were created with transcription effector-like nucleases (TALENs) that target exon 2 of the CD47 gene—TALEN constructs generously provided by James Chen. The TALEN constructs were introduced into either the DLD1 or SW620 line using the Nucleofector Kit L (Lonza). Briefly, 5 million cells of DLD1 cells were trypsinized, washed with PBS and resuspended in 100 μL of Nucleofector Solution along with 5 μg of purified TALEN plasmids. The cell suspension was transferred to a cuvette and electroporated using T-020 program on the Nucleofector II Device (Lonza). Transfected DLD1 cells were recovered from the cuvette with media and transferred onto 10 cm plates for culturing.

Single-Cell Sorting. To select for a pure knockout population, the cells electroporated with the TALEN constructs were then stained with APC-conjugated anti-CD47 antibody (clone B6H12) and sorted for cells that do not express CD47 on the surface using BD FacsAria III (BD Biosciences). After repeated attempts we were unsuccessful in verifying the CD47-knockdown by western as out of eight different CD47 clones available at the time none of them were able to recognize the denatured CD47 band transferred to the nitrocellulose membrane after SDS-PAGE—indicating that all the different antibody clones were conformational antibodies that recognized the properly-folded three-dimensional structure of the CD47 protein. Therefore, we decided to sort single cells from the population that was negative for CD47 cell-surface expression into 96-well plates. In our first few attempts we failed to expand the single cells in the 96 well plates after single cell sort. We hypothesized that single cells might need other secreted factors from the neighboring cancer cells to grow effectively. We therefore sorted single cells in 96-well plate that contained conditioned media, which is the filtered media aspirated from a confluent culture of the same cancer cell supplemented with serum. This time using the conditioned media we were able to expand the single cell clones. After growing multiple single cell clones to sufficient numbers we extracted total RNA and genomic DNA from each clone. We sequenced the CD47 cDNA after reverse transcription followed by PCR of the total RNA. As an added measure we also amplified the CD47 genomic locus spanning the CD47 exon 2 by PCR using the genomic DNA as template and primers that bound intron 1 and intron 2 and verified the disruption of CD47 coding sequence (frameshift) after sanger sequencing of the amplified PCR product.

Western Blot. Single cell clones of DLD1 knockout were expanded in 6-well plates. Cells were lysed using 100 μl Laemmli buffer pre-heated to 95° C. Proteins in the cell lysate were resolved using 12% SDS-PAGE gel using 15 μL of cell lysate per lane. 200 ng of purified CD47 protein was used as a positive control. The resolved proteins on the SDS-PAGE gel was transferred to a nitrocellulose membrane in CAPS buffer pH 11.0 using BioRad wet transfer apparatus at 100 V for 1.5 hours.

The nitrocellulose membrane with the transferred proteins was blocked in TBST with 5% non-fat dry milk. After blocking the membrane was incubated with primary anti-CD47 antibodies at 1:1000 dilution (in TBST with 5% non-fat dry milk) for 1 hour at room temperature. The membrane was washed 5 times with TBST, each wash being for 5 minutes to remove the unbound primary antibody. The membrane was then incubated for 1 hour with HRP-conjugated secondary antibody at a 1:10,000 dilution again in TBST with 5% non-fat dry milk. HRP (horseradish peroxidase)-mediated chemiluminescence on the membrane was activated by incubating the membrane with hydrogen-peroxide, p-coumaric acid and luminol for 1 minute before exposing the luminescent membrane to a photographic film in the dark room for various amounts of time (5 seconds to 20 minutes) followed by film development to visualize the protein bands. Primary anti-CD47 antibodies used: eBioscience 14-0478-82, eBioscience 14-0479-82, Abcam ab193940, and Abcam ab108415.

Creating CD47 null cell lines that express specific CD47 isoforms. Lentiviral constructs were designed to re-introduce specific CD47 splice-variants of interest back into the CD47-knockout cell lines. The lentiviral element (the element that integrates to the mammalian genome after infection by lentiviral particles) within the lentiviral constructs from 5' to 3' consists of a PGK promoter driven cDNA of either CD47 isoform 1 or isoform 2, followed by stop codon, followed by HCV-IRES, followed by ZsGreen cDNA, followed by T2A self-cleaving peptide, and finally followed by luciferase cDNA (Luc2). The use of HCV-IRES and T2A elements ensure that the CD47 isoforms have no N- or C-terminal fusions even when all three genes are expressed from a single transcript. This is essential as the N-terminus of CD47 is involved with extracellular interactions with its SIRPα receptor and the function of the C-terminal cytoplasmic tail is under investigation in the current study.

The lentiviral constructs were transfected into human embryonic kidney 293T cells (ATCC) along with the VSVG and PsPax2 packaging vectors in serum-free DMEM media (Life Technologies). The lentiviral transfection mix consisted of 11.5 ug of CD47 plasmid DNA, 11.5 ug of PsPax2, and 5 ug of VSVG suspended in 1 mL of serum-free media supplemented with 75 uL of polyethylenimine (PEI). The transfection mixture was incubated for 15 minutes at room temperature before applying directly drop-by-drop onto confluent plates of 293T target cells. Serum-free media was replaced with DMEM media supplemented with 10% FBS and 1% Penicillin and Streptomycin after 6 hours.

The supernatant (media above adherent 293T cells) containing the lentiviral particles was collected from the 293T plates at 12 hour intervals—each time after virus collection the transfected 293T cells were replenished with fresh media for further viral production. Lentiviral supernatant was filtered with 0.22 μm Millipore Steriflip filters (Fisher Scientific) to filter out any 293 cells that may have carried along and was mixed with polybrene (Sigma Aldrich) before adding directly to 40-50% confluent target cells (DLD1 or SW620 CD47-knockout cancer cells) for infection. The infection with procedure was repeated thrice to boost the transduction efficiency with each infection spaced 12 hours apart. Transduced DLD1 cells were verified with flow cytometry for expression of GFP (zsGreen) and cell-surface CD47 (APC-conjugated anti-CD47, clone B6H12).

CD47 Protein Immunofluorescence and Trafficking. DLD1 cells were grown to sparsely on 22×22-mm glass coverslips in 6-well dishes and fixed with 2% formaldehyde in PBS for 15 minutes at room temperature. Cells were permeabilized with 0.2% Triton X-100 (Sigma Aldrich) and 1% normal goat serum (NGS) (Abcam). Cells were washed three times in PBS for 10 minutes with caution to make sure that the cells did not dry out during aspiration. 1:1000 dilution of KDEL-Cy3 and CD47-AlexaFluor647 (clone B6H12) antibodies diluted in PBS containing 1% NGS were used to target the ER/Golgi complexes and CD47 proteins, respectively. Antibody incubation was done for 1 hour at 37° C. and 95% humidity. After incubation with antibodies, cells were washed with PBS and mounted onto microscope slides (VWR) with Fluormount-G (Southern Biotech) and imaged using a confocal microscope (Carl-Zeiss).

Mice Injections. 2 million cells of DLD1 parental, knock-out, isoform 1 and isoform 2 were diluted in 50 µL of PBS. Cells were gently transferred to and mixed in 100 µL of Matrigel Matrix (Corning) on ice. Subcutaneous injection of non-scid-gamma (NSG) mice were performed on the dorsal side along the coastal margin. 5 mice (ages 6-8 weeks) were allocated to each cell line and treatment condition. Mice that died prior to DLD1 injection were not included in the final data set.

Treatments of PBS control or 0.5 mg of anti-CD47 antibody (clone hu5F9G4) were delivered at 48 hour intervals via interperitoneal injection at 200 µL volume per injection. Mice were imaged weekly after 200 µL interperitoneal injections of luciferin diluted in PBS. Caliper measurements were recorded weekly as well to monitor tumor growth where the total area of the tumor was calculated following width and length measurements of the tumor.

Results

Figure 1B:
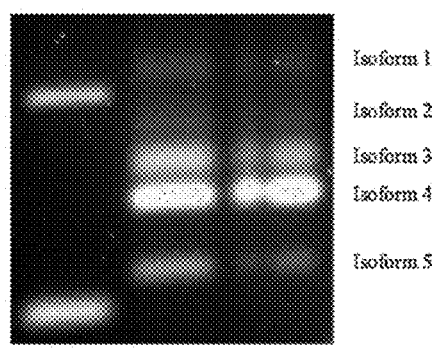
Figure 1C:
Figure 1D:
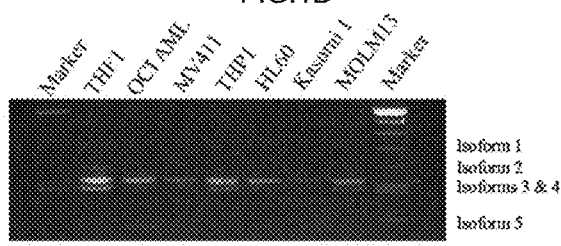
Figure 1E:
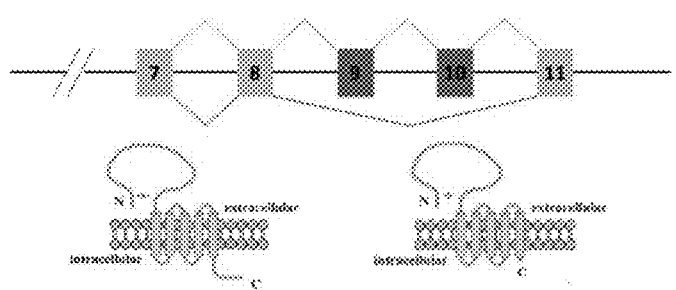

Characterization of CD47 Splice-Variants in hematologic and Solid Cancers. Human CD47 is known to have multiple mRNA isoforms in the region spanning exons 7 to 11, which corresponds to the cytoplasmic carboxy-C-terminal portion of the protein (FIG. 1A). Preliminary work in our lab had identified five different isoforms of CD47 in two different acute myeloid leukemia cancer cell lines, MOLM13 & THP1 (FIG. 1B). To confirm the presence of multiple mRNA isoforms in other cancer cells, we performed RT-PCR on hematologic and solid cancers. Using primers directed towards the variable cytoplasmic domain, we found the presence of five different CD47 isoforms in an expanded assay on various acute myeloid leukemia cancer cell lines (FIG. 1C-1D). We also found the presence of multiple isoforms in primary and metastatic colorectal cancer lines, DLD1 and SW620 (FIG. 1E). We decide to focus on two prominent isoforms: the full-length "Isoform 1" containing all exons 1-11, and a truncated "Isoform 2" that lacks exons 9 and 10 (FIG. 1F). Exons 9 and 10 correspond to the cytoplasmic domain of CD47. Thus, we believe the loss of the cytoplasmic domain in the truncated isoform may yield a different response to anti-CD47 antibody treatments.

Transient Expression of CD47 Splice-Variants. To test the response of the full-length and truncated CD47 isoforms to anti-CD47 treatment, we sought to overexpress our isoforms of interest in CD47-knockout cancer cell lines and observe the efficiency of phagocytic clearance of the cancer cells. The full-length and truncated isoforms were cloned from commercially available cDNA libraries into a pcDNA3.1 (+) mammalian expression vector driven by the strong mammalian cytomegalovirus (CMV) promoter for high-level expression (FIG. 2A). StbI3 competent cells were transformed with our pcDNA vectors containing either the full-length or truncated isoform. Phenol-chloroform nucleic acid extraction allowed us to quickly screen for StbI3 bacterial colonies that contained pcDNA plasmid with our inserted isoform sequence (FIG. 2B). Candidate colonies were selected for DNA sequencing of the cloned insert and were verified to contain our isoforms of interest.

Transfection of DLD1-knockout cells resulted in high surface expression of CD47 as evident from our flow cytometry data after staining with anti-CD47 antibodies (clones B6H12 and 2D3) (FIG. 2C). Phagocytosis assay performed by co-culturing with human macrophages with the transfected DLD1 cells with or without anti-CD47 antibody (clone B6H12) treatment yielded inconclusive results with regards to the efficacy of the two splice-variants as don't eat-me signal (FIG. 2D). This may have been due to the low transfection efficiency that may have resulted in not all cancer cells expressing the transfected CD47 splice-variant. The results may have been further confounded by the presence of all other endogenous splice-variants of in these cancer cells. After further investigation we detected that up to 5-16% of CD47 knock-out cells expressed low amounts of CD47 on the cell surface (data not shown). This CD47 knock-out DLD1 cell line was derived from a pool of sorted cells that stained negative for CD47 surface expression after the parental DLD1 cells were transfected with TALENS targeting the exon 2 of CD47 gene. Relying solely on FACS to isolate CD47 null cells does not rule out the possibility of a rare cell clone that still has CD47 expression. It is conceivable that such a clone, after a few passages may result in the 5-16% cells that we observed t have low CD47 expression. Further FACS based isolation of CD47 null cells does not remove cells that have a variant of CD47 that remains in the cytoplasm and not present on the surface. As a result, we needed to create a clean CD47 knockout line that did not express any version of CD47 isoforms. Only then, we would be able to study the function of individual CD47 isoforms this time by stably expressing them with the help of lentiviral constructs in the clean knockout cells.

Figure 3A:
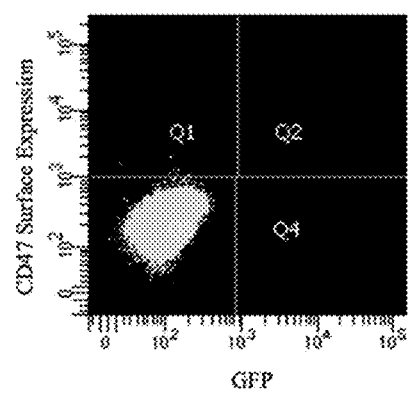
FIG. 3A-3B.
Figure 3B:
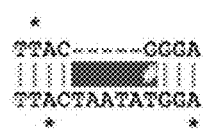

Establishment of DLD1 CD47-knockout Line. Using wildtype parental DLD1 cells, we induced double-strand breaks in the CD47 gene using TALENs directed towards exon 2. Cells were then sorted for the lack of CD47 expression on the cell surface using anti-CD47 antibodies (clones B6H12) (FIG. 3A). We attempted to use Western blots to confirm knockout of CD47 protein expression, but none of the commercially-available clones of CD47 antibodies were able to detect the denatured form of CD47 (see Materials and methods). Therefore, we resorted to performing single-cell sort to find a DLD1 cell clone that had a clear genetic lesion disrupting CD47 expression. After screening 12 such cell clones derived from single cells we uncovered a knockout candidate that had a 5-basepair insertion in exon 2 resulting in a frameshift as verified by DNA sequencing thus resulting in expression of a non-functional heavily truncated N-terminal CD47 peptide (FIG. 3B).

Figure 4A:
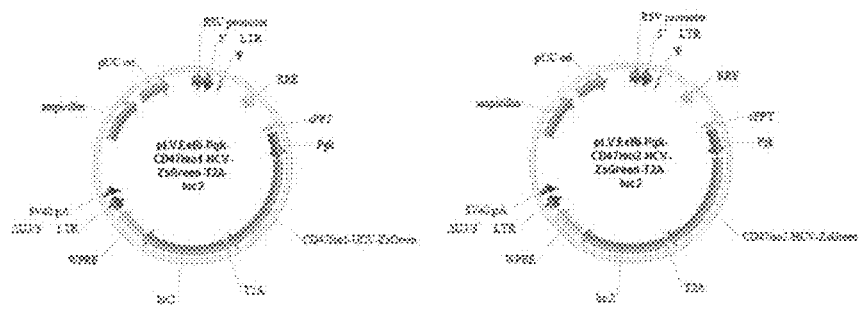
FIG. 4A-4C.

Stable Expression of CD47 Splice-Variants. Lentivirus constructs were created to stably express our two isoforms in the newly established DLD1 CD47KO and the SW620 CD47KO cell lines. We used a strong PGK promoter to aid in the production of our isoform. Because we are studying the effect of the cytoplasmic tail, we used HCV-IRES to avoid the fusion of the CD47 C-terminus with ZsGreen (GFP). HCV-IRES allows for translation to restart at the ZsGreen sequence to form a ZsGreen-T2A-Luciferase fusion. T2A is a self-cleaving peptide which releases separate ZsGreen (GFP variant) and luciferase. GFP will be useful in tracking the injected cancer cells when performing histology of tumor formed in mouse models after injection or flow cytometric analysis of the tumor cell suspension. Luciferase was included for live imaging for monitoring the growth of tumor in in vivo mouse models after injection (FIG. 4A).

Figure 4B:
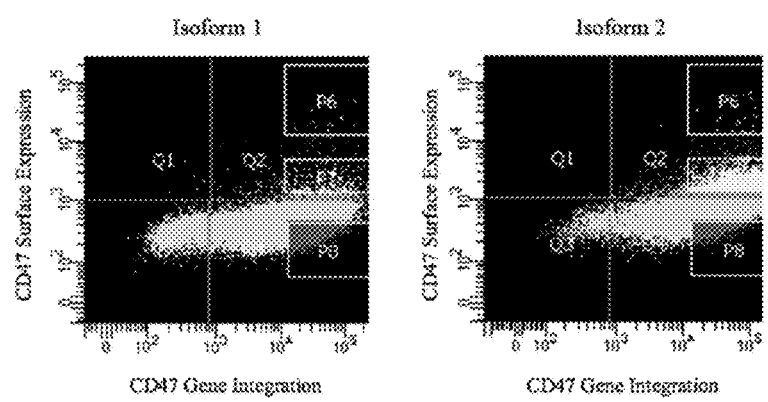
Figure 4C:
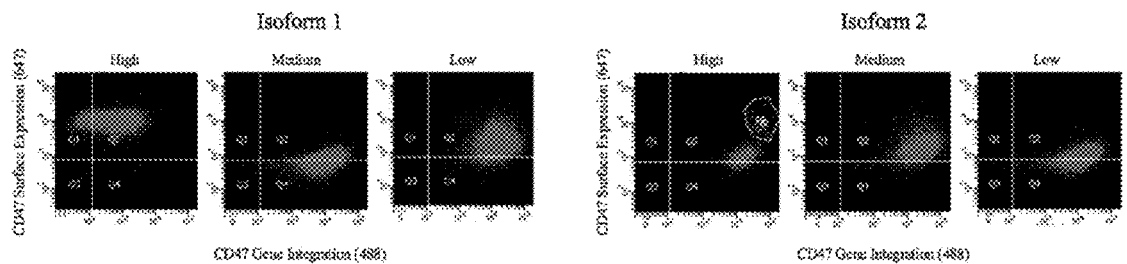

We transfected 293T cell lines with our lentivirus constructs along with VSVG & PsPax2 lentiviral packaging vectors and subsequently transduced our DLD1 CD47KO cell lines with the media containing the viral particles collected from the 293T cultures. Although the transduction efficiency was very high as evident from the high GFP expression in the majority of the cells, not all cells were able to produce surface expression of CD47 (FIG. 4B). Since CD47 and GFP were expressed from the same transcript, it seemed highly likely that CD47 isoforms were expressed but were not able to traffic to the cell surface. Further, in the cells transduced with the short isoform cDNA, it appeared that a higher fraction of cells appeared to have surface expression than the pool of cells transduced with the full-length isoform. We hypothesized that this was either due to a transient cell cycle effect or an epigenetic consequence of lentiviral integration at specific location(s) along the genome. To test this, we sorted the transduced cells into three different populations with high, medium, and low CD47 cell surface expression. This was done for both cells transduced with short and the long isoform. After propagating the cells over several weeks, we found stable CD47 surface expression for the full-length isoform (FIG. 4C). High expression populations maintained high CD47 surface expression, medium expression populations maintained medium CD47 surface expression, and low expression populations maintained low CD47 surface expression. It is unclear why GFP expression gradually subsides. For the short isoform, low and medium expression populations remained stable but the high expression population had segregated into high and medium expression clusters. We believe that this was due to impurities during the initial sorting and re-sorted for high CD47 surface expression. Throughout an additional four weeks of propagation, flow cytometric analysis showed that the expression of CD47 on the surface of the cells was stable. DLD1 parental (wildtype) and DLD1 CD47KO lines were also transduced with GFP for visualization in FACS analysis of subsequent phagocytosis assays.

Figure 5A:
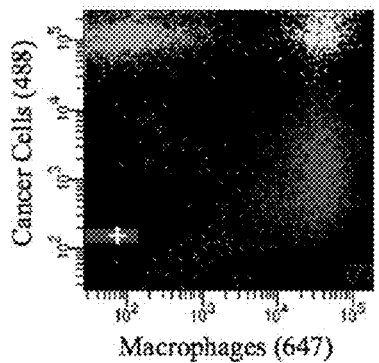
FIG. 5A-5E.

Anti-CD47 Phagocytosis. Parental, knockout, and our two isoforms of interest were incubated with antibodies for 30 minutes and co-cultured with human macrophages for 2 hours before flow cytometric analysis. For our phagocytosis assays, we employed proper fluorescence compensation and strict gating (FIG. 5A). Phagocytic activity was calculated as the number of double-positive macrophages—those which have eaten cancer cells—as a percentage of the number of total macrophages.

Using IGG4 antibody as a non-specific control and cetuximab antibody as a control for opsonization, we treated the cancer cells with a variety of anti-CD47 antibody treatments: 2D3 antibody binds to CD47 but does not block the CD47-SIRPα interaction while hu5F9G4 antibody binds to CD47 and blocks the CD47-SIRPα interaction. CV1, MB, and CV1G4 represent purified binding domains of the SIRPα receptor and also serve to block the CD47-SIRPα interaction. CV1 exists as a monomeric fragment while MB consists of two identical SIRPα binding domains connected together by a soluble linker. CV1G4 is similar to the dimeric MB with the addition of a conjugated Fc region. KWAR does not bind to CD47, but rather acts as an antagonistic ligand to block the SIRPα receptor on macrophages. We elected to use the high CD47 surface expression populations of DLD1 for these assays assuming that they would exhibit the clearest distinctions between the two isoforms in terms of function.

Figure 5B:
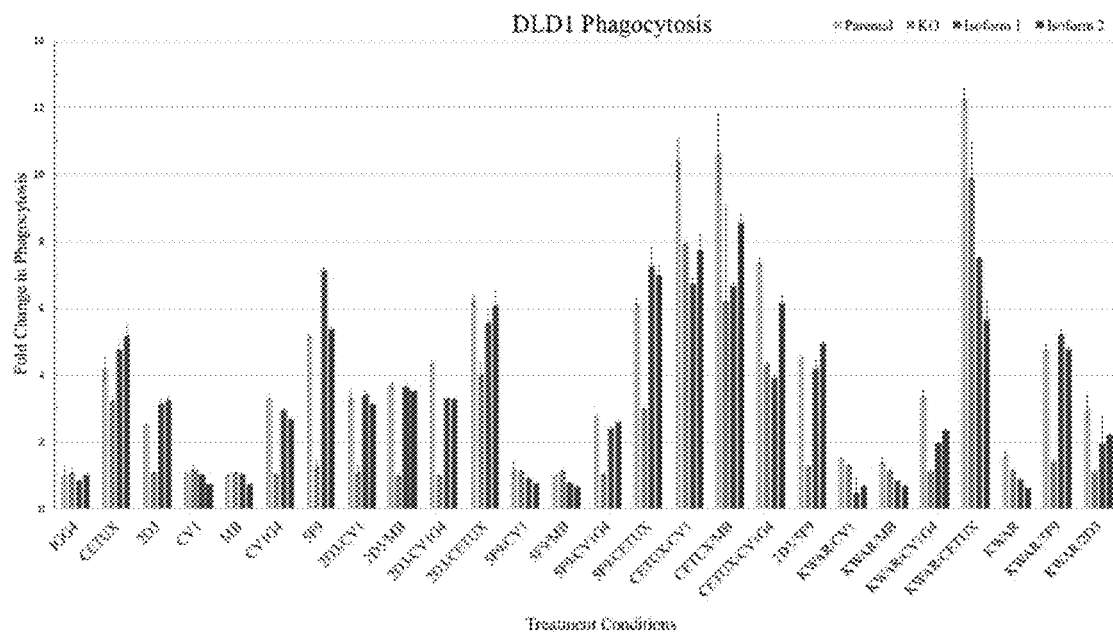

In our phagocytosis assays with DLD1 and its engineered variants, we observed that anti-CD47 antibody treatment works primarily through a strong opsonization effect (FIG. 5B). Treatments that contain Fc regions yield high levels of phagocytosis of DLD1 cancer cells expressing either the full-length or truncated isoforms. Interestingly, treatments that block the CD47-SIRPα interaction yet lack an antibody Fc region (CV1, MB, KWAR) have negligible effects on phagocytic clearance and may even competitively repress the opsonization effect of anti-CD47 antibody treatment as seen in the reduction of phagocytosis in 2D3 and hu5F9G4 treatments when combined with CV1, MB, or KWAR.

Figure 5C:
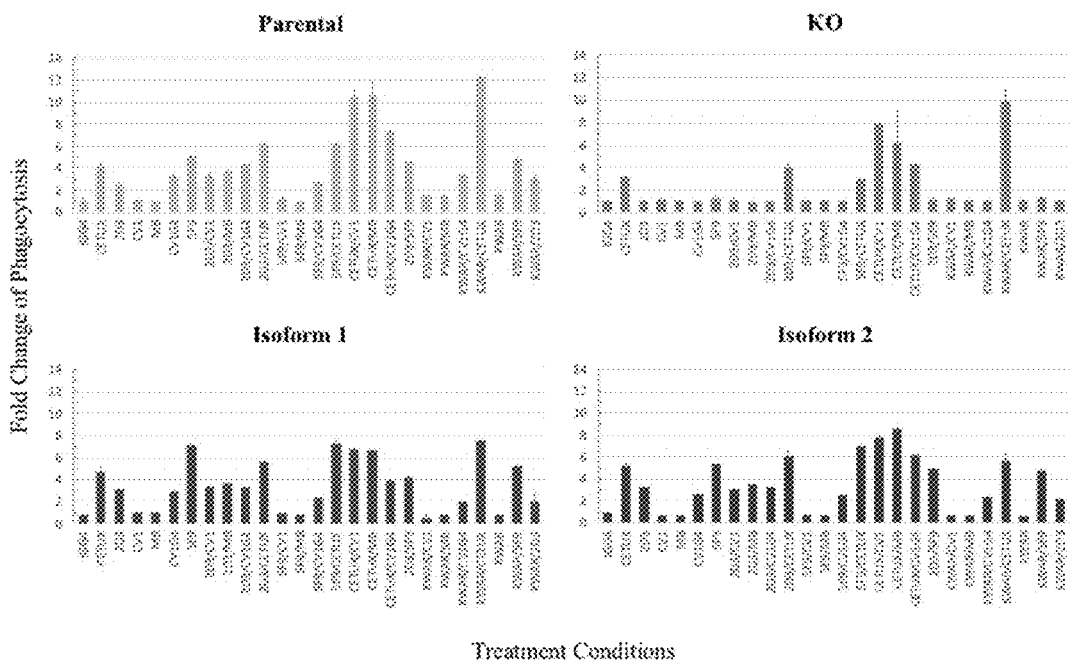

Analyzing each cell line individually, the full-length and truncated CD47 isoforms both appear to have similar responses to our battery of treatment conditions (FIG. 5C). The full-length isoform is more responsive to hu5F9G4 and KWAR/CETUX treatment while the truncated isoform responds better to CETUX/CV1, CETUX/MB, and CETUX/CV1G4. However, across the board, both isoforms respond comparably to the different treatment conditions. Because the parental line expresses both the full-length and truncated isoforms, it expectedly has treatment responses that parallel the data observed for the cell lines transduced with our isoforms of interest.

Furthermore, as expected, the CD47 knockout line only had increased phagocytosis following cetuximab treatments since it lacks CD47 expression and, therefore, does not gain the opsonization effect of anti-CD47 antibody therapy.

Figure 5D:
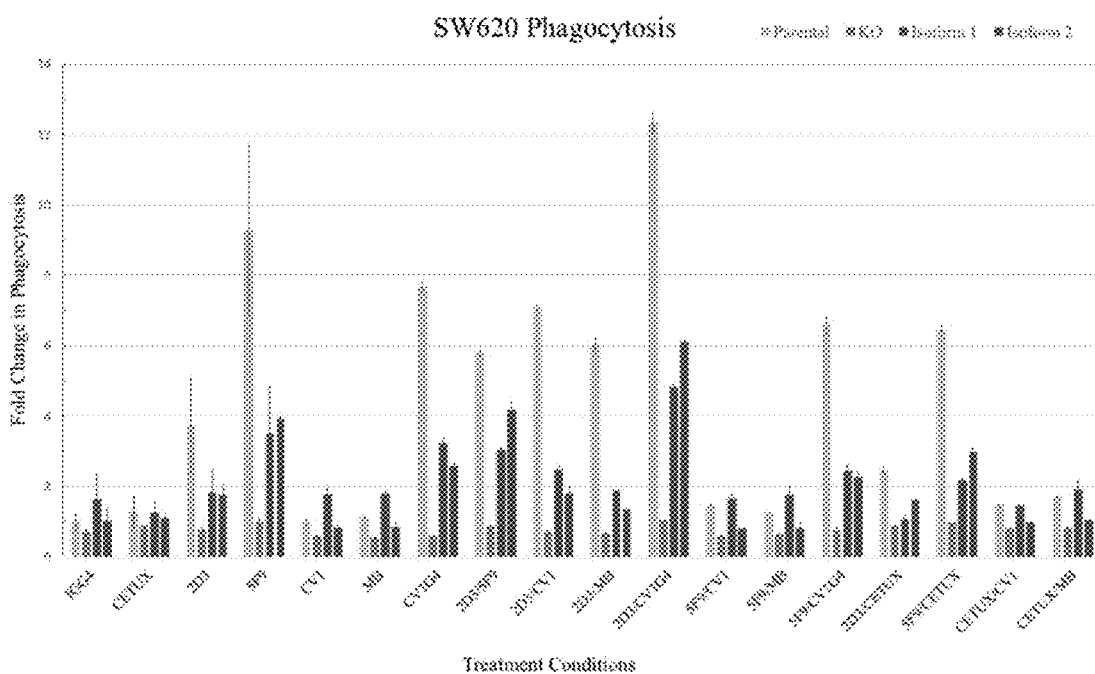
Figure 5E:
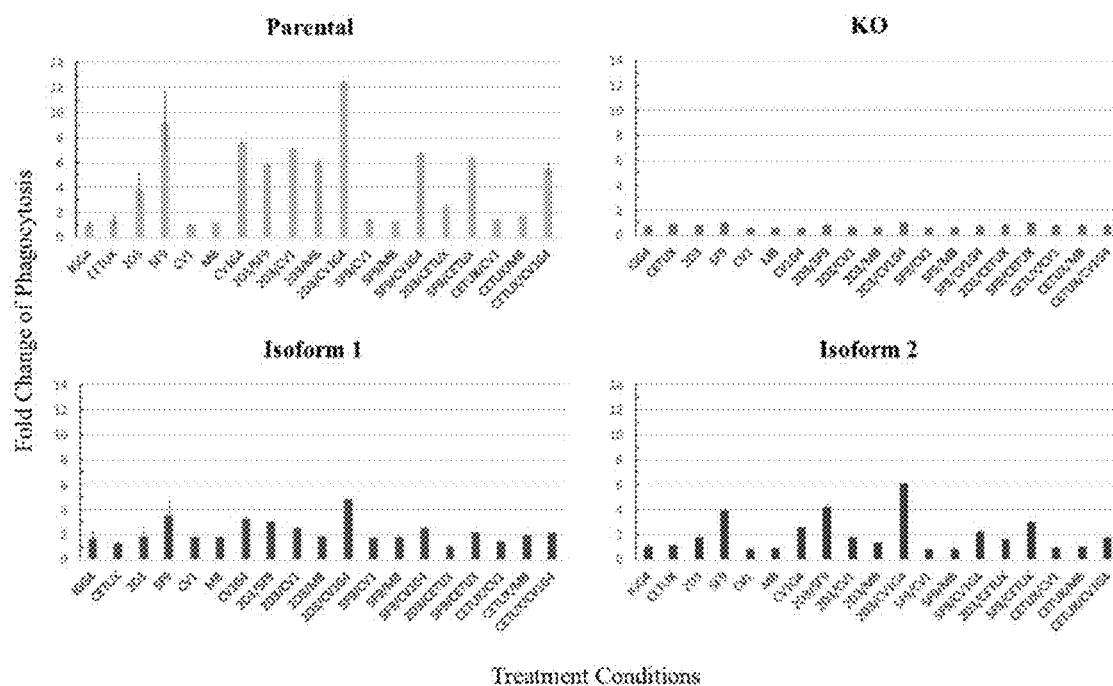

We extended our investigation with a metastatic colorectal cancer line, SW620. An SW620 knockout cell line was obtained and, just as we had done with DLD1, was transduced with our two isoforms of interest. SW620 parental, knockout, full-length CD47-expressing, and truncated CD47-expressing cancer lines were similarly treated for 30 minutes before co-culturing with human macrophages for 2 hours. Because SW620 lacks EGFR expression, we saw no increased cancer cell clearance in cetuximab treatment conditions unlike what we saw with DLD1 (FIG. 5D). The phagocytic clearance of SW620 cancer cells expressing either the full-length or truncated CD47 isoform is as expected with respect to the treatment conditions and in line with data collected from DLD1 cells. Treatments that only inhibit the CD47-SIRPα interaction yield negligible differences in phagocytosis as compared to the PBS and IGG4 controls. Across both isoforms, treatments with antibodies that contain Fc regions to confer opsonization lead to the highest levels of phagocytosis. Although both isoforms have similar response patterning, the full-length isoform has a more blunted response to the anti-CD47 treatments with an average of 2.205±0.904 fold increase of phagocytic activity over baseline as compared to the truncated isoform's more accentuated response with an average of 1.990±1.425 fold increase.

Figure 6A:
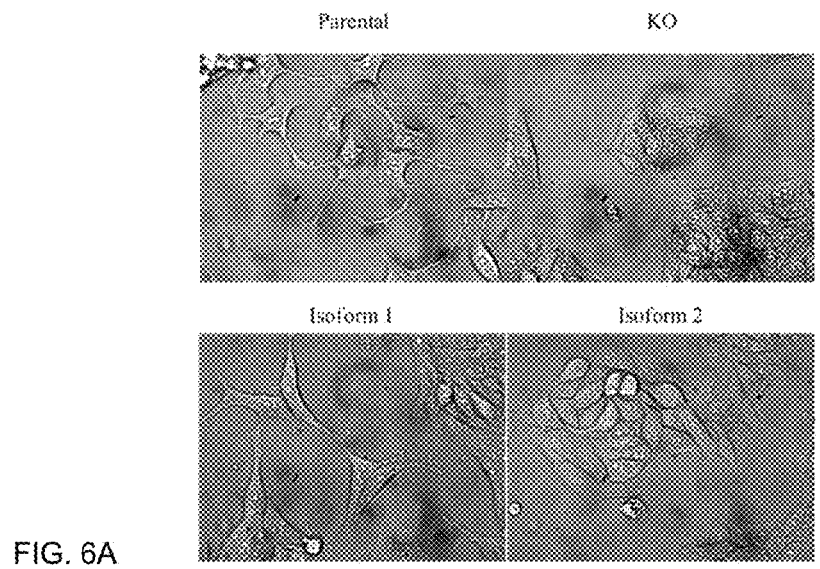
FIG. 6A-6B.

Visualization of DLD1 Morphology and CD47 Protein Localization. To see if the selective expression of either full-length or truncated CD47 confers macro-level differences in cancer cells, we compared the morphology of DLD1 parental, knockout, Isoform 1, and Isoform 2. Phase-contrast microscopy shows the full-length Isoform 1 exhibiting filopodium-like protrusions similar to the DLD1 parental lines (FIG. 6A). Truncated Isoform 2 exhibits fewer protrusions as does DLD1 KO. The formation of filopodium-like protrusions is purported to be the rate-limiting step in the progression to metastasis as cancer cells interact more with the extracellular matrix during their epithelial-mesenchymal transition (EMT)[27]. The protruding morphology of Isoform 1 may suggest a propensity for its proliferation and migration out of primary cancer tissue. Isoform 2, with its lack of filopodium-like protrusions, may exhibit a slower growth rate.

Figure 6B:
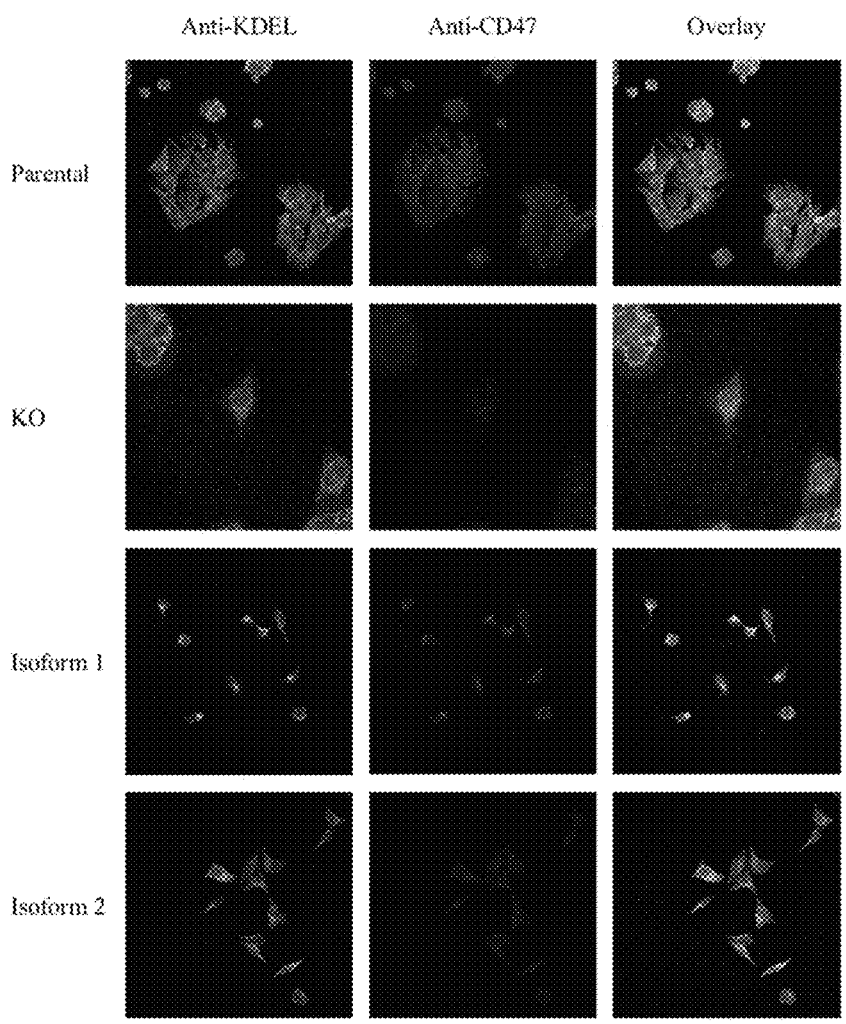

Looking more specifically at CD47, we fixed samples of our DLD1 cell lines and incubated them with anti-KDEL and anti-CD47 (clone B6H12) to observe the intracellular trafficking of CD47 protein to the cell surface. We see appropriate staining of the ER/Golgi complexes, located midway between the nucleus and the cell membrane. We also notice that the full-length CD47 isoform localizes to the cell surface with greater efficiency than the truncated isoform (FIG. 6B). Isoform 2 has fewer CD47 protein molecules trafficking to the cell surface and the uniform distribution of CD47 within the cells suggests that the truncated isoform of CD47 is trapped within the ER/Golgi complexes.

Figure 7A:
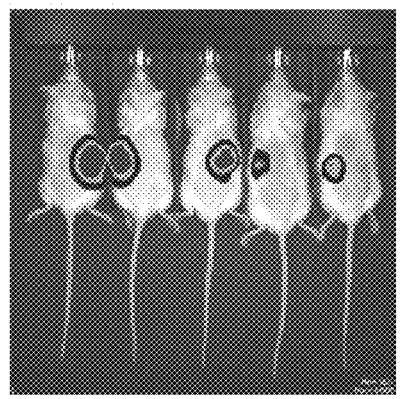
FIG. 7A-7E.

Xenotransplantation of DLD1 in NSG Murine Models. Based on the observations of distinctive morphologies and CD47 protein trafficking in DLD1 cells expressing Isoform 1 or Isoform 2, we believed that the different functions of the two isoforms may occur at a macroscopic level and were not readily observable through our in vitro phagocytosis assays. We proceeded by injecting 2 million DLD1 cells from parental, knockout, Isoform 1, and Isoform 2 cell lines to the dorsal side of NSG mice. The mice were treated with 500 µg of anti-CD47 antibodies (clone hu5F9G4) every 2 days and imaged weekly via luciferase bioluminescence. Immediately after the first imaging time point (one-week post-injection), we found that the injected cell count was too high. By the first time point, the DLD1 xenografts had engrafted and proliferated so rapidly that luciferase bioluminescence had already reached saturation, thus preempting the ability to track tumor growth with bioluminescence imaging (FIG. 7A).

Figure 7B:
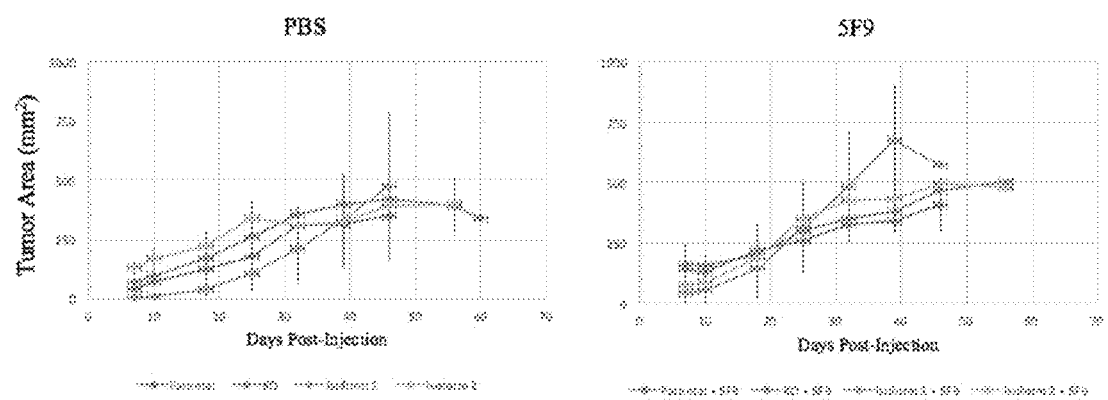

Unable to assess tumor burden through imaging, we manually took weekly caliper measurements of the growing tumors. When segregated into treated versus untreated cohorts, there was no significant difference in the proliferation rates of the four DLD1 cell lines (FIG. 7B). This coincides with our conclusion from the oversaturated imaging data that the high number of injected cells limited the ability of the innate immune system (macrophages) to have a noticeable impact in clearing out the cancer cells. Under normal circumstances, we would have expected DLD1 KO to have significantly slower growth due to its lack of the inhibitory CD47-SIRPα interaction.

Figure 7C:
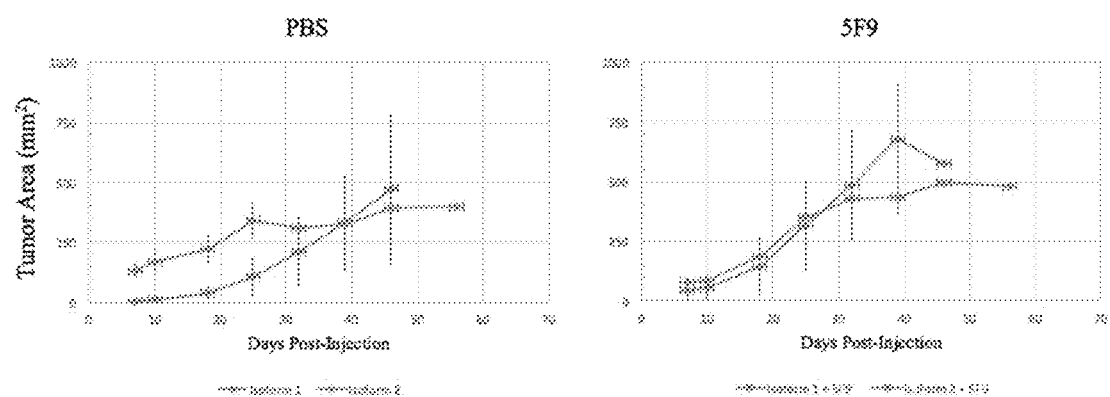
Figure 7D:
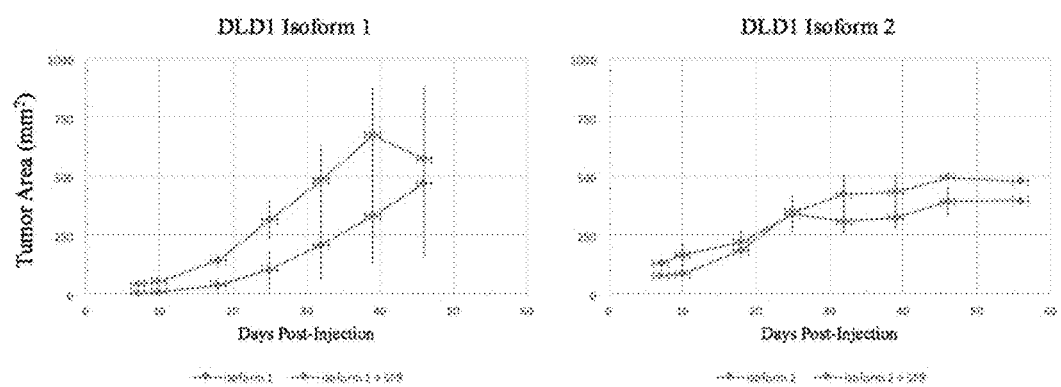
Figure 7E:
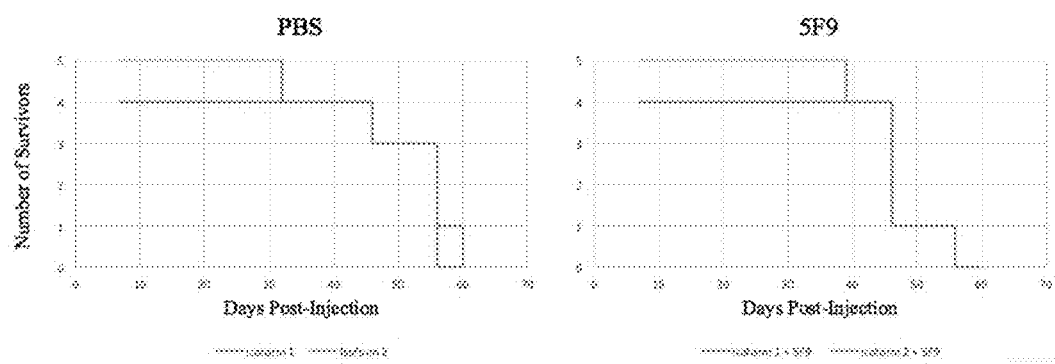

Interestingly, although the final tumor size of Isoforms 1 and 2 are similar, full-length Isoform 1 exhibits a much more aggressive proliferation curve when untreated with anti-CD47 antibodies as compared to the steady growth of the truncated Isoform 2 population. Treatment with anti-CD47 therapy tames the proliferation rate of Isoform 1 such that it follows closely with the growth of Isoform 2 (FIG. 7C). In evaluating individual isoforms and their response to anti-CD47 treatment, there is no significant effect of the treatment therapy on their growth rate (FIG. 7D). There were also no significant differences in the survivability of Isoform 1 or 2 when treated with PBS or anti-CD47 antibodies (clone 5F9) (FIG. 7E). These observations strongly suggest that the tumors had grown too rapidly for meaningful response by the innate immune system and future in vivo experiments should inject fewer cells.

The overexpression of CD47 in cancerous cells as well as its traditional function of inhibiting macrophage-mediated phagocytosis lends itself as an ideal marker for targeted cancer therapy. Because multiple isoforms of CD47 are co-expressed in wildtype cancer cells, our selective expression of either the full-length isoform 1 or the truncated isoform 2 in clean CD47 knockout cells allowed us to clearly compare each isoform's response to anti-CD47 antibody therapy.

Although blocking the CD47-SIRPα interaction led to slightly higher phagocytosis due to the abolishment of CD47's inhibitory effects, we were surprised to see that the major benefit of anti-CD47 antibody therapy is via the opsonization effect through the Fc region of the antibodies. Treatments that only block the CD47-SIRPα interaction can augment antibody treatments that do not block CD47 signaling. However, combinatory treatments that compete for the CD47-SIRPα binding domain are less effective that the prescription of a singular anti-CD47 antibody treatment. This observation suggests that anti-CD47 cancer therapy is best served if drug cocktails utilize non-competitive inhibitors that block the CD47-SIRPα interaction and opsonize the cancer cell to recruit phagocytic macrophages.

We did not observe a significant difference in the responses of CD47 Isoform 1 or Isoform 2 to our battery of treatment conditions through in vitro phagocytosis assays. However, the distinct cell morphologies and surface expression of CD47 between the two populations suggest that CD47 may have secondary higher-order functions that were not readily visible at the cancer cell-macrophage level. For example, the greater propensity for filopodia-like protrusions due to full-length CD47 expression may confer a faster rate to metastasis for cancers that exhibit higher ratios of Isoform 1 to Isoform 2. Such ability would be an addition to the canonical function of CD47 in decreasing or inhibiting the phagocytic clearance of cancer cells.

BIBLIOGRAPHY

Hanahan, D., & Weinberg *Cell,* 144(5), 646-674 (2011).
Chan et al. *Proc Natl Acad Sci USA* 106, 14016-21 (2009).
Chao et al. *Curr Opin Immunol* 24, 225-32 (2012).
Edris et al. *Proc Natl Acad Sci USA* 109, 6656-61 (2012).
Kim et al. *Leukemia* 26, 2538-45 (2012).
Majet et al. *Cell* 138, 286-99 (2009).
Willingham et al. *Proc Natl Acad Sci USA* 109, 6662-7 (2012).
Chao et al. *Cancer Res* 71, 1374-84 (2011).
Chao et al. *Sci Transl Med* 2, 63ra94 (2010).
Chao et al. *Nat Rev Cancer* 12, 58-67 (2012).
Gardai et al. *Cell* 123, 321-34 (2005).
Mateo et al. *Nat Med* 5, 1277-84 (1999).
Matlin et al. *Nat Rev Mol Cell Biol* 6, 386-98 (2005).
Chao et al. *Sci Transl Med* 2, 63ra94 (2010).
Chao et al. *Nat Rev Cancer* 12, 58-67 (2012).
Oldenborg et al. *Science* 288, 2051-4 (2000).
Kharitonenkov et al. *Nature* 386, 181-6 (1997).
Fujioka et al. *Mol Cell Biol* 16, 6887-99 (1996).
Timms et al. *Mol Cell Biol* 18, 3838-50 (1998).
Tsai et al. *J Cell Biol* 180, 989-1003 (2008).
Tseng et al. *Proc Natl Acad Sci USA* Accepted (2013).
Black et al. *Annu Rev Biochem* 72, 291-336 (2003).
Karn et al. *Nat Struct Mol Biol* 14, 185-93 (2007).
Singh et al. *Trends Mol Med* 18, 472-82 (2012).
Chao et al. *Cell* 142, 699-713 (2010).
Reinhold et al. *Journal of cell science,* 108(11), 3419-3425 (1995).
Shibue et al. *Cancer discovery,* 2(8), 706-721 (2012).
Zheleznyak et al. *Molecular imaging,* 12(8) (2013).

What is claimed is:

1. A method of treating an individual responsive to an anti-CD47 agent, the method comprising:
    assaying a cell sample from an individual to measure the levels of two or more CD47 isoforms,
    determining that the individual is responsive to the anti-CD47 agent when the level of a CD47 isoform comprising a cytoplasmic tail is present at a ratio of at least 1:10 relative to other CD47 isoforms, and
    administering an anti-CD47 agent to the responsive individual.

2. The method of claim 1 wherein the CD47 isoform comprising a cytoplasmic tail is present at a ratio of at least 1:10 relative to CD47 isoform 2 in the cell.

3. The method of claim 1 wherein the biological sample is one or more of a blood sample, a serum sample, a plasma sample, a biopsy sample, a fine needle aspirate, a lymph node aspirate, a cystic aspirate, a paracentesis, and a thoracentesis sample.

4. The method of claim 1, wherein the assaying step comprises measuring protein levels of CD47 isoforms.

5. The method of claim 1, wherein the assaying step comprises measuring the level of mRNA of CD47 isoforms.

6. The method of claim 5, wherein measuring the level of mRNA comprises performing a method selected from the group consisting of: a hybridization-based method, a polymerase chain reaction (PCR)-based method, and a nucleic acid sequencing method.

* * * * *

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Synthetic nucleotide

<400> SEQUENCE: 1
gagatgtggc ccctggtag                                                  19

<210> SEQ ID NO 2
<211> LENGTH: 40
<212> TYPE: DNA
<213> ORGANISM: Artificial sequence
<220> FEATURE:
<223> OTHER INFORMATION: Synthetic nucleotide

<400> SEQUENCE: 2
atcacttcac ttcagttatt cattaagggg ttcctctaca                           40

<210> SEQ ID NO 3
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 3
tgaacaatgg aaatgttgct g                                               21

<210> SEQ ID NO 4
<211> LENGTH: 40
<212> TYPE: DNA
<213> ORGANISM: Artificial sequence
<220> FEATURE:
<223> OTHER INFORMATION: Synthetic nucleotide

<400> SEQUENCE: 4
atcacttcac ttcagttatt cattaagggg ttcctctaca                           40